(12) United States Patent
Meyer et al.

(10) Patent No.: US 9,619,613 B2
(45) Date of Patent: *Apr. 11, 2017

(54) DEVICE AND METHODS FOR MOBILE MONITORING AND ASSESSMENT OF CLINICAL FUNCTION THROUGH SENSORS AND INTERACTIVE PATIENT RESPONSES

(71) Applicant: Integrated Deficit Examinations, LLC, Rancho Santa Fe, CA (US)

(72) Inventors: Brett C. Meyer, San Diego, CA (US); Justin A. Zivin, Rancho Santa Fe, CA (US)

(73) Assignee: Integrated Deficit Examinations, LLC, Rancho Santa Fe, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,162

(22) Filed: Oct. 19, 2015

(65) Prior Publication Data

US 2016/0042123 A1 Feb. 11, 2016

Related U.S. Application Data

(63) Continuation of application No. 13/921,997, filed on Jun. 19, 2013, now Pat. No. 9,171,131.
(Continued)

(51) Int. Cl.
*G06F 19/00* (2011.01)
*A61B 5/00* (2006.01)
(Continued)

(52) U.S. Cl.
CPC .......... *G06F 19/321* (2013.01); *A61B 5/0022* (2013.01); *A61B 5/16* (2013.01);
(Continued)

(58) Field of Classification Search
None
See application file for complete search history.

(56) References Cited

U.S. PATENT DOCUMENTS 5,363,859 A * 11/1994 Tuckett et al. ............... 600/552
6,406,426 B1 6/2002 Reuss et al.
(Continued)

OTHER PUBLICATIONS

International Preliminary Report on Patentability mailed on Dec. 4, 2014 received in International Application No. PCT/US13/46869.
(Continued)

*Primary Examiner* — William Thomson
*Assistant Examiner* — Davin Sands
(74) *Attorney, Agent, or Firm* — Knobbe Martens Olson & Bear LLP

(57) ABSTRACT

Methods and systems are disclosed for sensing and assessing a patients responses to tests using a device that may include tactile input, voice input, still image analysis, and responses to visual and auditory stimuli. In one example, a method includes obtaining interactive clinical assessment data using a remote client device and a computer-based control device, the method including providing on a display of a remote client device one or more test prompts for conducting an interactive clinical assessment, each displayed test prompt instructing a user to perform an action using the remote client device in response to the test prompt, and providing on the display of the remote client device one or more potential responses of actions that may be performed in response to the test prompt.

20 Claims, 18 Drawing Sheets

Related U.S. Application Data

(60) Provisional application No. 61/663,478, filed on Jun. 22, 2012.

(51) Int. Cl.
*A61B 5/16* (2006.01)
*A61B 5/11* (2006.01)
*A61B 5/22* (2006.01)

(52) U.S. Cl.
CPC ............ *A61B 5/225* (2013.01); *A61B 5/4076* (2013.01); *A61B 5/4082* (2013.01); *A61B 5/4088* (2013.01); *A61B 5/6898* (2013.01); *A61B 5/7271* (2013.01); *A61B 5/74* (2013.01); *A61B 5/742* (2013.01); *A61B 5/7405* (2013.01); *A61B 5/7455* (2013.01); *G06F 19/3418* (2013.01); *G06F 19/363* (2013.01); *A61B 5/1121* (2013.01); *A61B 5/224* (2013.01); *A61B 5/4005* (2013.01); *A61B 2560/0443* (2013.01); *A61B 2560/0475* (2013.01); *A61B 2562/0204* (2013.01); *A61B 2562/0247* (2013.01)

(56) References Cited

U.S. PATENT DOCUMENTS

| | | | | |
|---|---|---|---|---|
| 6,540,663 | B1* | 4/2003 | Vau et al. | 600/27 |
| 8,016,416 | B1* | 9/2011 | Straus | 351/200 |
| 8,179,418 | B2 | 5/2012 | Wright et al. | |
| 2003/0059759 | A1* | 3/2003 | Calhoun et al. | 434/322 |
| 2003/0117485 | A1* | 6/2003 | Mochizuki et al. | 348/14.01 |
| 2005/0187436 | A1* | 8/2005 | Doniger et al. | 600/300 |
| 2007/0119248 | A1 | 5/2007 | Lee | |
| 2007/0164997 | A1* | 7/2007 | Gruber | 345/163 |
| 2007/0225578 | A1* | 9/2007 | Howell et al. | 600/306 |
| 2009/0070144 | A1 | 3/2009 | Haider | |
| 2009/0259339 | A1 | 10/2009 | Wright et al. | |
| 2009/0270775 | A1* | 10/2009 | Tommerdahl et al. | 601/70 |
| 2009/0298025 | A1* | 12/2009 | Raber | 434/236 |
| 2010/0113979 | A1 | 5/2010 | Sarrafzadeh | |
| 2010/0169409 | A1* | 7/2010 | Fallon et al. | 709/203 |
| 2010/0191375 | A1 | 7/2010 | Wright et al. | |
| 2011/0013004 | A1 | 1/2011 | Nieminen | |
| 2011/0065550 | A1* | 3/2011 | Cohn et al. | 482/8 |
| 2011/0070835 | A1 | 3/2011 | Borras et al. | |
| 2011/0118559 | A1* | 5/2011 | Aharonson | 600/300 |
| 2012/0077163 | A1* | 3/2012 | Sucar Succar et al. | 434/247 |
| 2012/0178063 | A1* | 7/2012 | Bristow et al. | 434/236 |
| 2012/0179226 | A1* | 7/2012 | Graham et al. | 607/77 |
| 2012/0190947 | A1* | 7/2012 | Chon et al. | 600/323 |
| 2012/0255355 | A1* | 10/2012 | Xu et al. | 73/379.02 |
| 2013/0130218 | A1* | 5/2013 | Hargreaves | 434/362 |

OTHER PUBLICATIONS

International Search Report dated Mar. 28, 2014 received in International Application No. PCT/US13/46869.

Anderson, et. al; Remote assessment of stroke using the iPhone 4; J Stroke Cerebrovasc Dis. May 2013;22(4);340-4.

Kim DK, et al; A mobile telemedicine system for remote consultation in cases of acute stroke; J Telemed Telecare. 2009;15(2:102-7.

NIH Stroke Scale. Oct. 1, 2003.

Supplementary Search Report mailed on Mar. 23, 2016 in European Application No. 13737017.7, filed on Jun. 20, 2013.

* cited by examiner

When prompted, if lying flat, hold your arm straight out at a 45 degree angle to the bed. If sitting upright, hold your arm straight out parallel to the bed. A picture of these two choices is shown below. Hold the device there for 10 seconds, and then lower it.

4

Hold!

FIG. 11

In a few moments, this device will begin to vibrate. Indicate when you feel the vibrations by touching the button below.

Press this button when a vibration occurs.

DEVICE AND METHODS FOR MOBILE MONITORING AND ASSESSMENT OF CLINICAL FUNCTION THROUGH SENSORS AND INTERACTIVE PATIENT RESPONSES

CROSS REFERENCE TO RELATED APPLICATIONS

This application is a continuation of U.S. patent application Ser. No. 13/921,997, filed Jun. 19, 2013, which claims the benefit of U.S. Provisional Application No. 61/663,478, filed Jun. 22, 2012, each of these applications titled "DEVICE AND METHOD FOR MOBILE MONITORING AND ASSESSMENT OF CLINICAL NEUROLOGICAL FUNCTION THROUGH SENSORS AND INTERACTIVE PATIENT RESPONSES," and each of these applications are incorporated by reference herein in its entirety.

BACKGROUND

Field of the Invention

This disclosure relates generally to a mobile clinical assessment device itself, the methods for controlling the mobile clinical assessment device and the technology for performing these relevant clinical deficit assessments. More specifically, but not by way of limitation, this disclosure relates to devices, systems and software for facilitating the analysis and reporting of both directly and indirectly entered clinically relevant neurologic parameters, and numerically outputting the presence or absence of neurologic deficit worsening, utilizing a computing device similar in form and function to a smartphone.

Description of the Related Art

The current marketplace has numerous technologic devices aimed at quantifying and reporting physiologic data in the medical field. These devices are used in a wide array of settings and for various clinical uses such as home monitoring, inpatient hospital physiologic monitoring, or even monitoring of clinical and physiologic parameters in the rehabilitation setting. All of these devices have in common the ability to monitor parameters and report them to an interpreting care provider.

Many of the monitoring devices currently available focus mainly on continuously or intermittently assessing physiologic parameters (such as electrocardiogram (ECG) tracings, pulse oxymetry, forced vital lung capacity, blood sugar monitoring results, etc.). Clinical parameters are usually not included as they often require significant interaction with the patient to obtain clinical assessment data. Physiologic data monitoring is simpler and lends itself to more streamlined reporting of results.

Limitations of the prior art utilizing transmission of electrical signals such as ECG or EEG tracings include focusing on the physiologic parameters and not on meaningful clinical deficit examinations. Other applications fail to provide a reliable, inexpensive personal monitoring device that is readily compatible with existing computing devices where the clinical data can be compiled, analyzed and reported to a provider in clinically meaningful (and customizable) ways. It would be useful if the disadvantages of the prior art and other issues were addressed in a personal monitoring device configured to transmit real time clinical data.

SUMMARY

The systems, methods and devices of the disclosure each have several innovative aspects, no single one of which is solely responsible for the desirable attributes disclosed herein.

Some implementations of the current device are designed to solve the problem of not having an accurate and efficient device and methods for clinically determining the degree of patient neurologic deficit (other than frequent, detailed neurologic assessments performed by a neurologist), and/or being able to monitor for clinical worsening of patient's condition in a hospital or medical facility, or at a remote location including but not limited to a patient transport vehicle (for example, an ambulance) or the patients home. The described implementations can be used by a patient or a medical provider.

One innovative aspect described in this disclosure can be implemented in a mobile device for monitoring and assessing clinical neurological parameters of a patient, the device including at least one of means-for determining level or arousal, means-for determining gaze assessment, means-for determining pupil asymmetry, means-for determining visual fields, means-for determining facial asymmetry, mean-for determining the strength of motor functionality, means-for determining in-coordination, means-for determining touch sensory perception, means-for determining speech clarity or dysarthria, means-for determining language deficit aphasia, and means-for determining inattention/neglect assessments. The device can further include a wireless transmitter to communicate information indicative of neurological parameters and a user interface for inputting data into the device. In some implementations the information indicative of neurological parameters includes data collected from a sensed input from an action performed by the patient. The information indicative of neurological parameters can include sensed data collected indirectly from the patient. In some implementations, the information indicative of neurological parameters can include data input into the device through the user interface. The device can further include wireless transmitter and a receiver, or a transceiver.

Other innovative aspects of the subject matter described in this disclosure can be implemented in a mobile device for monitoring and assessing clinical neurological parameters of a patient, the device including a wireless transceiver to communicate information indicative of neurological parameters, a user interface for inputting neurological information into the device, motor sensory module, a voice recognition module, and an image recognition module. The motor sensory module can include at least one pressure sensor. In some implementations, the motor sensory module includes at least one accelerometer. The user interface can include a display, and the user interface module is configured to receive input and display data. The voice recognition module includes a microphone, and the voice recognition module can be configured to receive an audio input via the microphone and determine an assessment of dysarthria based on the audio input. The image recognition module can include an image sensing device, and the image recognition module can be configured to generate an image and determine an assessment of at least one of pupil asymmetry and facial asymmetry based on the generated image. In some implementations, the device is operable to calculate the validity of stimuli responses and numerically output the presence or absence of neurologic deficit or clinical worsening compared to prior examinations or programmed standards. The device can be configured to report a change in a monitored or sensed condition on a display screen, to report a change in a monitored or sensed condition to a mobile device, and/or to report a change in a monitored or sensed condition to a central monitoring station.

In some implementations, personal monitoring and assessment methods and devices (for example, a server-side control device and/or a remote client device) have a technology assembly designed to analyze both directly and indirectly entered patient data via motor control of device, tactile input, voice input, still image analysis, and responses to visual and auditory stimuli. The client device itself can contain sensors and hardware to assess relevant clinical neurologic parameters such as arousal, visual function, ability to follow commands, assessment of pupil size and function, facial topography, location of gaze, speech clarity, language correctness, understanding, motor positioning, motor strength, sensation, coordination and neglect. For example, to assess a visible characteristic of a patient, a client device may include an imaging device (e.g., a camera), and image analysis software that is configured to determine pupil size, location of gaze and/or facial topography. In some implementations, the client device collects images (for example, of a patient's face and eyes) and send the images to a control device (for example, a server-side control device) that is configured with image analysis programs, and the control device determines pupil size, location of gaze and/or facial topography from the received images. The images may be a portion of response information sent from the client device to the control device. Images can be collected and analyzed, in various implementations by the client device or the control device, as part of any of the patient assessments described herein, or for other assessments. Analogous to a clinical neurologic exam assessing for differences between a baseline neurologic examination and an examination showing neurologic worsening, this device is able to calculate the validity of stimuli responses and numerically output the presence or absence of neurologic deficit or clinical worsening compared to prior examinations or programmed standards. Reporting any change in function may be done directly on the device display screen, or using CDMA or EVDO cell-phone signal (or 802.11 wireless signals) to send a report to pager, cell phone or central monitoring station. Devices can be programmed to alert in any of these ways, if a numerical output is below a chosen threshold. The central monitoring station can track all tests and outputs. Frequency of assessments and output parameters can be changed either on the individual device or central monitoring station.

In some implementations, methods can include using a personal monitoring and assessment device to assess for clinical neurologic deficit and report when findings are outside of pre-programmed parameters.

In some implementations, a mobile monitoring and assessment terminal can allow for patient interface via touch sensitive screen display, virtual keyboard, other keyboard buttons, audio and video input. The personal monitoring device may have an assembly configured to receive input parameters from both direct and indirect patient entry. This assembly may analyze the input and produces electrical signals representing (electrically) the relevant clinical input.

In some configurations, a smartphone form-factor is provided. This form factor allows for a standard, familiar interaction between patient and device.

Some implementations of the assembly can be directly connected to a central computing element with storage media that analyzes these signals based on a pre-programmed threshold of findings, and compares it to prior baseline readings (and centralized standard findings). The computing process and storage media are provided for storing a set of instructions capable of being executed by one or more computing devices. This allows for the programming of standard scores for each item tested and normal ranges, allowing for comparisons between standard control results and individual patient baseline results. The computing device then can output these signals both to the device's touchscreen as a reporting of the results, through a wireless transmitter to a central monitoring station, and through cell phone signal to a care provider's pager or cell phone.

Some implementations include a method for interfacing with the mobile monitoring and assessment terminal. The method can include the steps of interfacing with the terminal via touchscreen, virtual keyboard, other keyboard buttons, audio and video input. The method also can include the steps of the terminal interfacing back with the patient via touchscreen, audio output, visual output and a sensory (vibration) output. This method allows for sensing of the input information, processing the data via computer processor, comparing the results to chosen and programmable standards, and alarming to the provider if these findings are outside of the range of acceptable limits.

In some implementations, a user interface provides a user with the ability to interact with a device in order to determine a clinical examination score. This interface may involve providing and recording responses to sensory stimuli, grading motor responses, recording and assessing speech samples, and recording and analyzing numerous still images for side to side comparisons and changes from baseline. Hence, information regarding the patient's clinical deficit may be recorded (with the assistance of direct and indirect patient interface) and reported as a numerical output. Any changes from baseline, outside of a pre-specified and programmable amount, can be signaled in an alarm to the healthcare provider, to the patient, or to a caregiver other than the healthcare provider (for example, a friend or relative caring for the patient at home).

This is advantageous in a number of ways, including the fact that it is usable in a wide range of clinical situations (for example, for patients with stroke, dementia, Parkinson's disease, cognitive impairment and Alzheimer's disease, or other conditions including other neurologic conditions that may predispose to neurologic worsening), it is as straightforward as the patient participating in a clinical examination provided by his/her care provider, and it has the most important advantage of being clinically superior to the current practice of nursing staff occasionally performing neurochecks on some small percentage of patients admitted to the hospital. For example, the client device described herein can be programmed to perform test to gather patient responses for the mini mental status exam (MMSE) for cognitive impairment and Alzheimer's disease, or the unified Parkinson's disease rating scale (UPDRS). In some implementations, the client device can be configured with other quantifiable scales for cardiology, neurology, or other tests related to disease, medicine or surgery for performing a variety of desired tests where patient interaction for clinical deficit scoring is used. In other words, the client device, and the system including the remote client device in communication with a control device, can be programmed to perform numerous interactive test on patients to help diagnose and test for a number of diseases, not limited to those described herein. Such tests can be designed to use any combination of the using sensors and components described herein, for example one or more of a pressure sensor, audio sensor (e.g., microphone), imaging sensor (e.g., camera), motion sensor (e.g., accelerometer), audio output component (e.g., speaker), one or more input buttons, a vibration component, a global positioning system, a communication component (e.g., a radio transceiver) and a display including a touchscreen display, as well as other suitable components such as a temperature sensor (e.g., thermometer). Some implementations may include a plurality of such sensors (for example, two or three pressure sensors).

The personal monitoring can be configured to be used by a wide array of patients with various types of severe neurologic deficit to still be able to participate in an examination (such as having an option where the patient does not have to hold the grip handle if the hand is too weak, but can place the hand through the handle to elevate the device). If necessary, the nursing staff could assist with the patient's performance of the exam in order to increase the number of patients who could benefit from this device. However, if the deficit is too severe, it is likely that this patient is less in need of interval assessments of neurologic worsening since he or she has already worsened to a great degree. In fact, the larger percentage of patients who can likely be using this device are those with mild to moderate degrees of deficit where the care provider is exquisitely focused on knowing if there is immediate deterioration in function (thus allowing for possibility of further intervention/patient salvage).

Other example innovations are now described. The different innovative aspects described below may be, in certain implementations, be used in conjunction with other implementations described herein, even if not specifically discussed for such implementations.

One innovation includes a method of obtaining interactive clinical assessment data using a remote client device and a computer-based control device, the method including providing on a display of a remote client device one or more test prompts for conducting an interactive clinical assessment, each displayed test prompt instructing a user to perform an action using the remote client device in response to the test prompt, and providing on the display of the remote client device one or more potential responses of actions that may be performed in response to the test prompt. The method may also include receiving input at the remote client device, the input indicative of an action performed in response to a test prompt provided on the display of the remote client device. The method may also include sending response information from the remote client device, the response information being indicative of input received at the remote client device in response to the one or more test prompts provided on the display of the remote client device. The method may also include receiving clinical tests at the remote device, and wherein the one or more test prompts are based at least in part on the received clinical tests. The method may also include clinical test parameters at the remote client device, and wherein the one or more test prompts are based at least in part on the received test parameters. The method may also include receiving patient information at the remote client device, and wherein the one or more test prompts are based at least in part on the received patient information. The method may also include receiving the response information sent by the remote client device at the control device, evaluating at the control device the response information, and determining the status of a patient based on evaluating the response information. The method may further include sending the clinical tests, sending the clinical test parameters, and/or sending the patient information from the control device to the remote client device. The method may include evaluating the response information to determine a change from baseline results of a particular patient. In some implementations, the method may include sending an alert signal from the control device based on a determined patient status. Such an alert signal may be sent to a computer, a pager, a smartphone or other mobile communication device, or be provided to a display where it can be displayed. In some examples, such an alert signal may be sent to an alarm device, for example, to indicate an alarm condition using a light or an audio output. The method may further include transmitting a series of tests, a series of parameters and a patient profile for responses from the control device to the remote client device, determining response information indicative of responses received at the remote client device, transmitting the response information to the control device, and evaluating the response information at the control device to determine a clinical status of a patient. In any of the methods described, receiving input may include receiving selection of a potential response that is provided on the display of the remote client device. The displays disclosed herein may be a touchscreen display. In some implementations, the display is a touchscreen and receiving input comprises receiving two or more selections from the display. In some implementations, receiving input may be receiving input from a sensor of the remote client device configured to sense pressure, from a sensor of the remote client device configured to sense movement of the remote client device, receiving an audio input, and/or receiving an input of one or more images. The method may also include communicating between the remote client device and the control device over a network, the communicating between the remote client device and the control device including wireless communication.

Another innovation includes a system of obtaining interactive clinical assessment data. The system can include a remote client device including a display, a memory unit configured to store test information that is sent to the remote client device, and a processor operationally coupled to the memory unit and the display, the processor configured to provide on the display one or more test prompts and one or more potential responses of actions to be performed in response to the test prompt. The system can further include a control device in communication with the remote client device. The control device may be configured to send the test information to the remote client device, and the remote client device configured to send response information to the control device, the response information based on input received at the remote client device. In some implementations, the test information includes at least one of clinical tests, clinical test parameters, or patient information. The system can include one or more sensors incorporated into the remote client device for receiving input in response to a displayed test prompt. For example, the system can include one or more sensors configured to sense pressure operationally coupled to the processor and where the processor is configured to receive a signal from the one or more sensors configured to sense pressure as input, one or more sensors configured to sense movement of the remote client device, one or more sensors including a microphone to sense an audio input and the processor is configured to receive the audio input, and/or one or more sensors including an electronic imaging circuit and the processor being configured to receive one or more images as input. In some implementations the system includes a global positioning system (GPS) circuit, and the processor is further configured to provide location information of the remote client device in response information provided by the remote client device. The remote client device may further include a speaker, and wherein the processor is further configured to provide, using the speaker, audio prompts and audio output in response to the remote client device receiving an input. The remote client device can further include a circuit configured to produce a vibration test prompt at the remote client device. The system can further include a circuit configured to send and receive wireless communications, and such a circuit can be incorporated in the remote client device, the control device, or both. In some implementations, the remote client device includes a communications circuit operationally coupled to the processor, the communications circuit configured to receive the test information, and wherein the processor is configured to provide the one or more test prompts and the one or more potential responses based on the received test information.

In some implementations of the systems described herein, the test information includes clinical test parameters, and the one or more test prompts are based at least in part on the received clinical test parameters. In some implementations of the systems described herein, the test information includes patient information, and the one or more test prompts are based at least in part on the received patient information. In some implementations of the systems described herein, the test information includes clinical tests to be performed on the remote client device, and wherein the one or more test prompts are based at least in part on the received clinical tests. The control device can include a processor configured to evaluate the response information received from the remote client device, and determine the status of a patient based on evaluating the response information. Such a processor can be configured to provide an alarm signal based on a determined patient status. The control device can include a processor configured to evaluate the response information received from the remote client device and determine a change from a baseline result associated with the same patient as the response information is associated with.

Another innovative aspect includes a non-transitory computer-readable medium comprising code that, when executed, causes an apparatus to provide on a display of a remote client device one or more test prompts for conducting an interactive clinical assessment, each displayed test prompt instructing a user to perform an action using the remote client device in response to the test prompt, and provide on the display of the remote client device one or more potential responses of actions that may be performed in response to the test prompt. The non-transitory computer-readable medium can also include code that performs other methods and functionality as described herein. In one example, the non-transitory computer-readable medium includes code that when executed further causes an apparatus to receive a series of tests, a series of parameters and a patient profile, receive input from one or more sensors in response to displaying the one or more test prompts, determine response information indicative of the received input, and send the response information to a control device for evaluation.

Another innovation includes a system of obtaining interactive clinical assessment data, the system including means for providing on a display of a remote client device one or more test prompts for conducting an interactive clinical assessment, each displayed test prompt instructing a user to perform an action using the remote client device in response to the test prompt, and means for providing on the display of the remote client device one or more potential responses of actions that may be performed in response to the test prompt. The system may further include means for receiving a series of tests, a series of parameters and a patient profile communicated from a control device, means for receiving input from one or more sensors in response to displaying the one or more test prompts, means for determining response information indicative of the received input, and means for sending the response information to the control device for evaluation. The system may further include means for receiving response information form the remote client device, means for evaluating the response information, and means for determining the status of a patient based on evaluating the response information. The system may further include means for determining a series of tests, a series of parameters and a patient profile, and means for communicating the a series of tests, a series of parameters and the patient profile to the remote client device to conduct a deficit assessment.

BRIEF DESCRIPTION OF THE DRAWINGS

Figure 1:
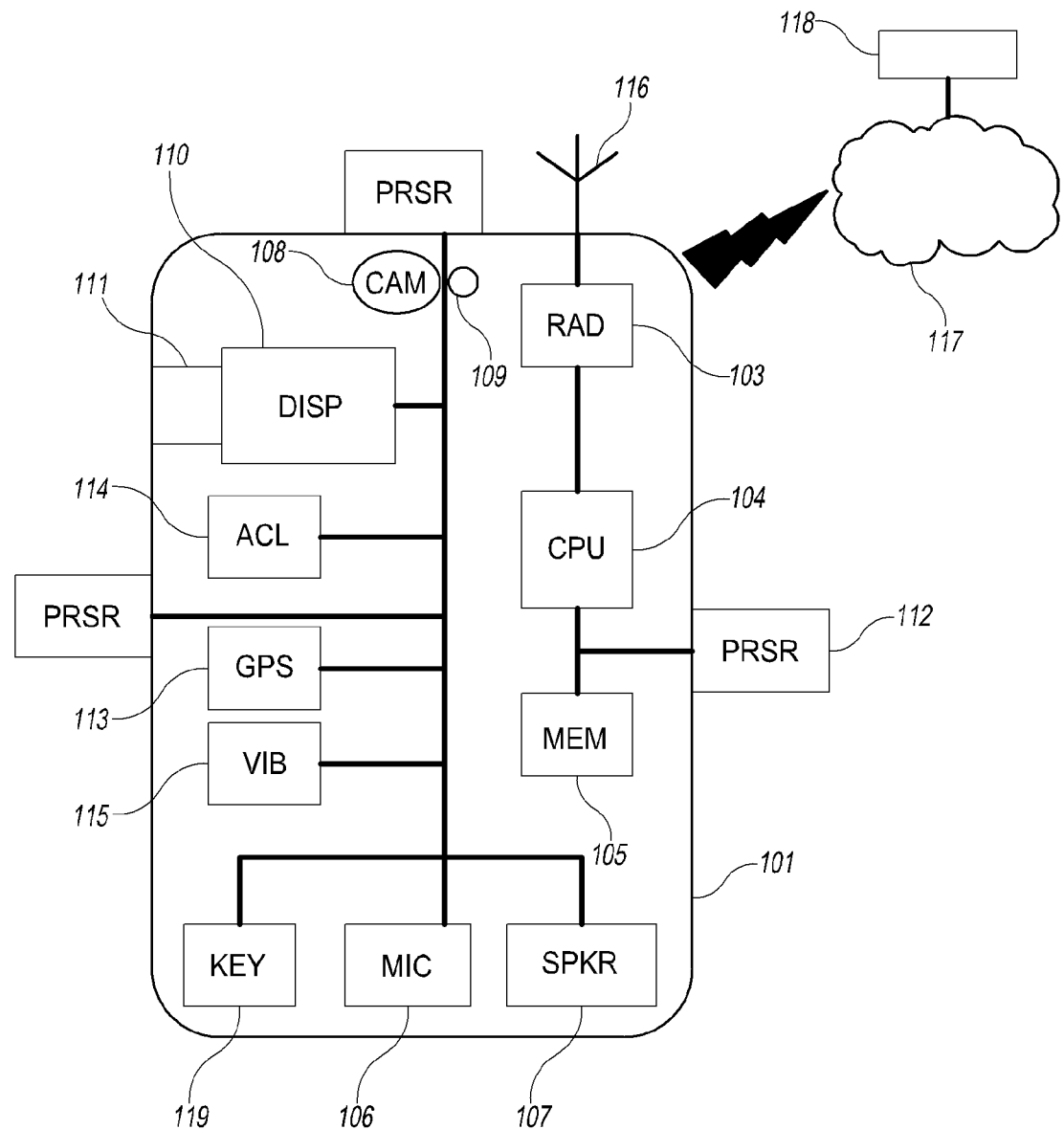

Having thus described certain aspects of the invention in general terms, reference can now be made to the accompanying drawings, which are not necessarily drawn to scale, and wherein:

FIG. 1 shows schematically a block diagram of a clinical assessment device according to one implementation of the present invention. Circuitry is not illustrated to be an accurate representation of an actual circuit pattern, instead being an example of component integration.

Figure 2A:
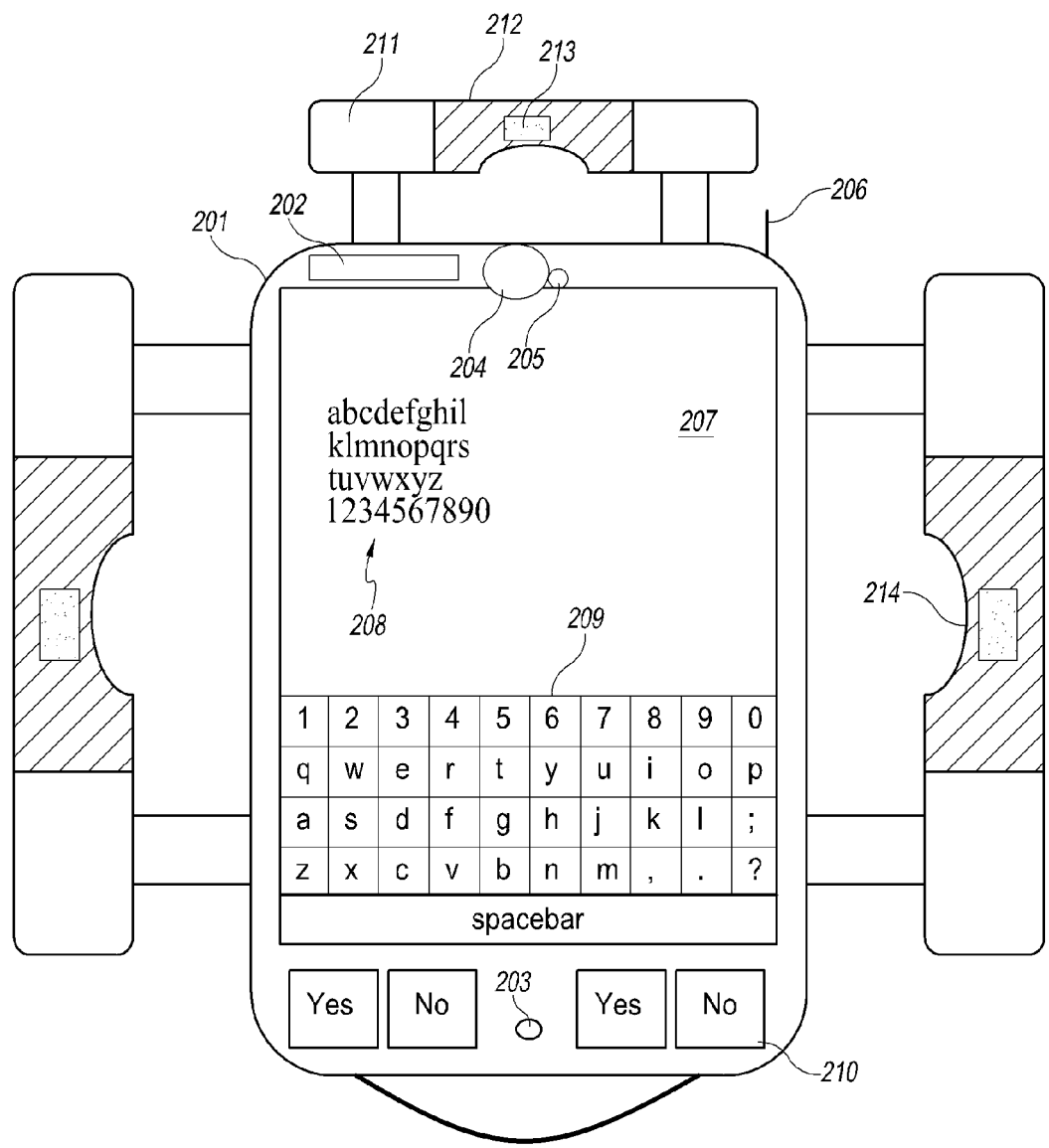

FIG. 2A. illustrates the external appearance of the clinical assessment device itself, noting particularly its external features, onscreen keyboard and text display.

Figure 2B:
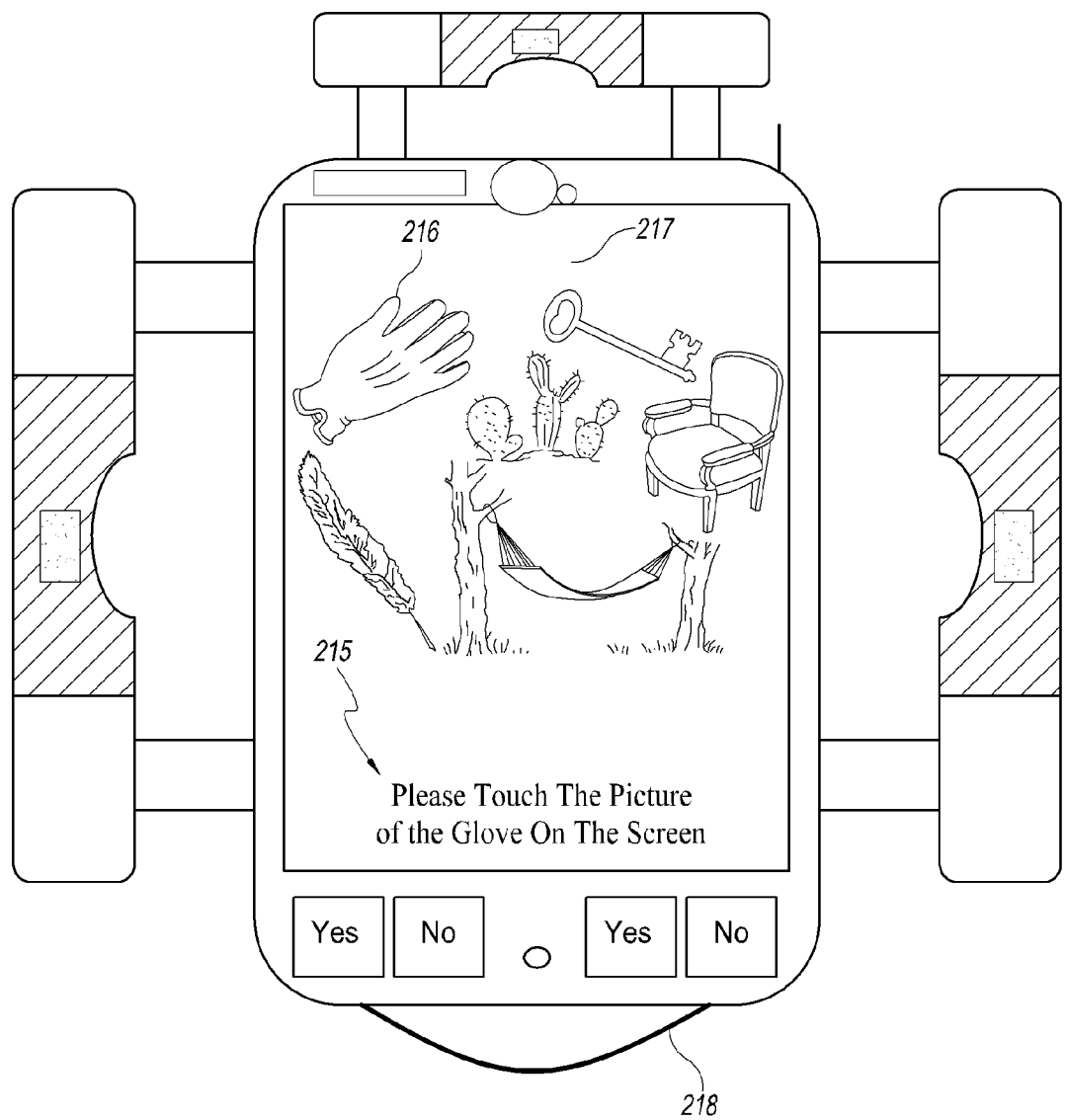

FIG. 2B. illustrates the external appearance of the clinical assessment device itself, noting particularly some of its onscreen functionality (including touchscreen video display and text instructions).

Figure 3:
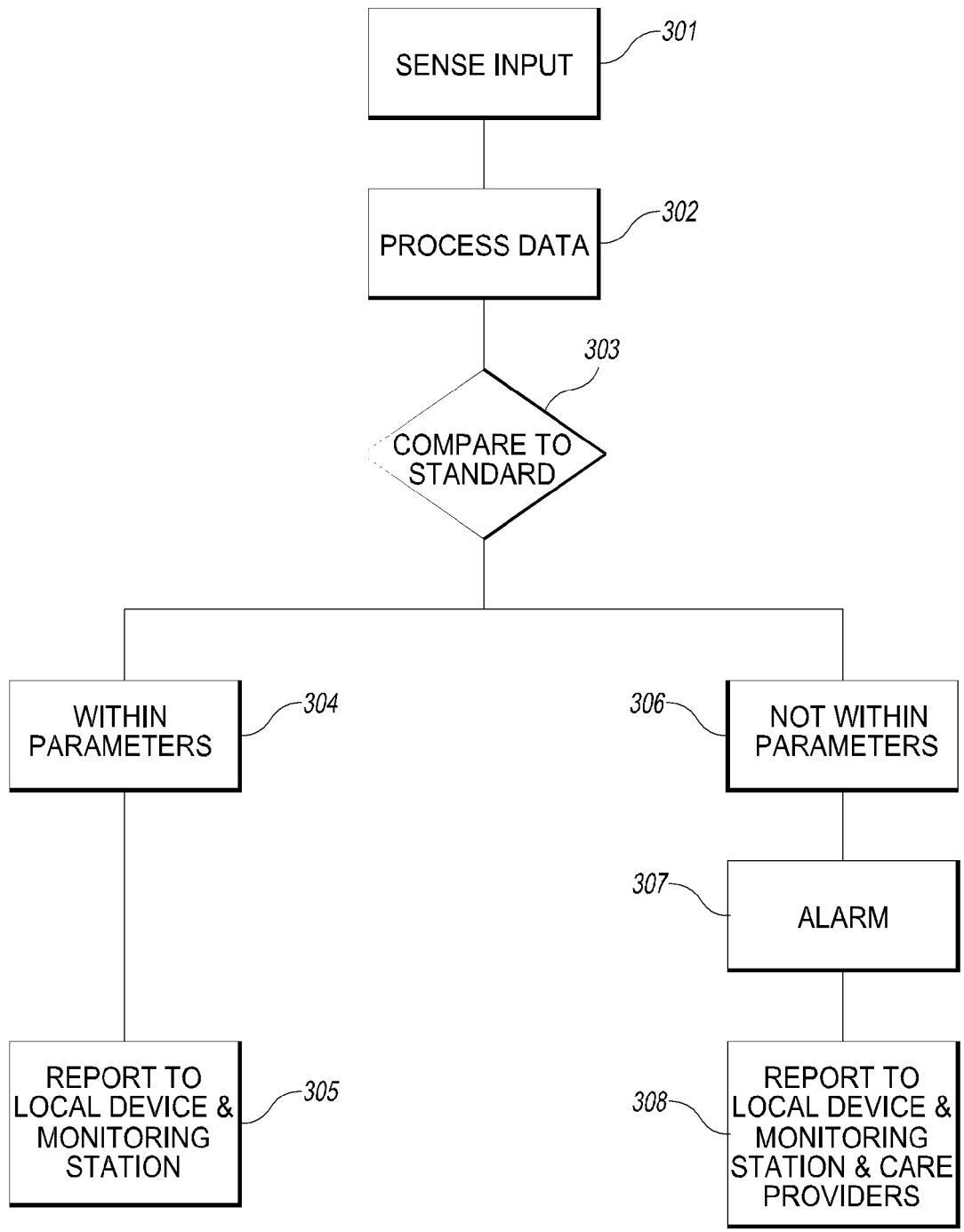

FIG. 3 is a flow chart illustrating a process according to one implementation of the present invention.

Figure 4:
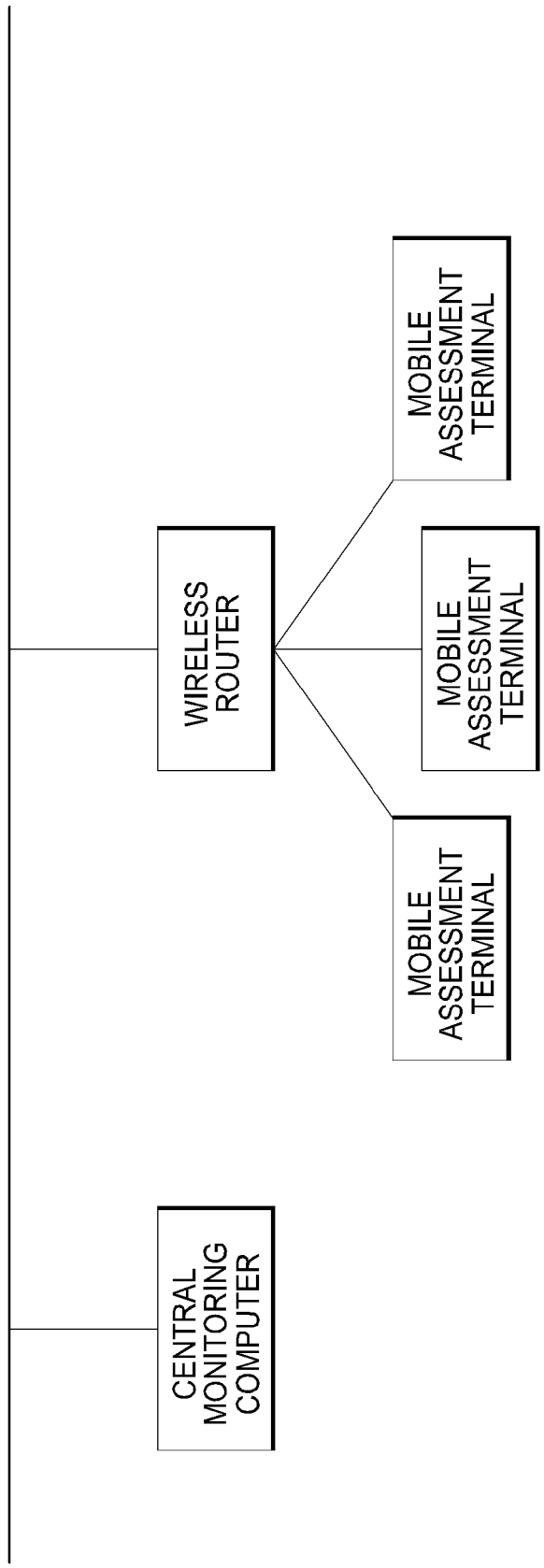

FIG. 4 is an architecture diagram of a clinical assessment configuration consisting of a central monitoring computer and multiple mobile assessment terminals connected by a wireless connection, according to one implementation of the present invention.

Figure 5:
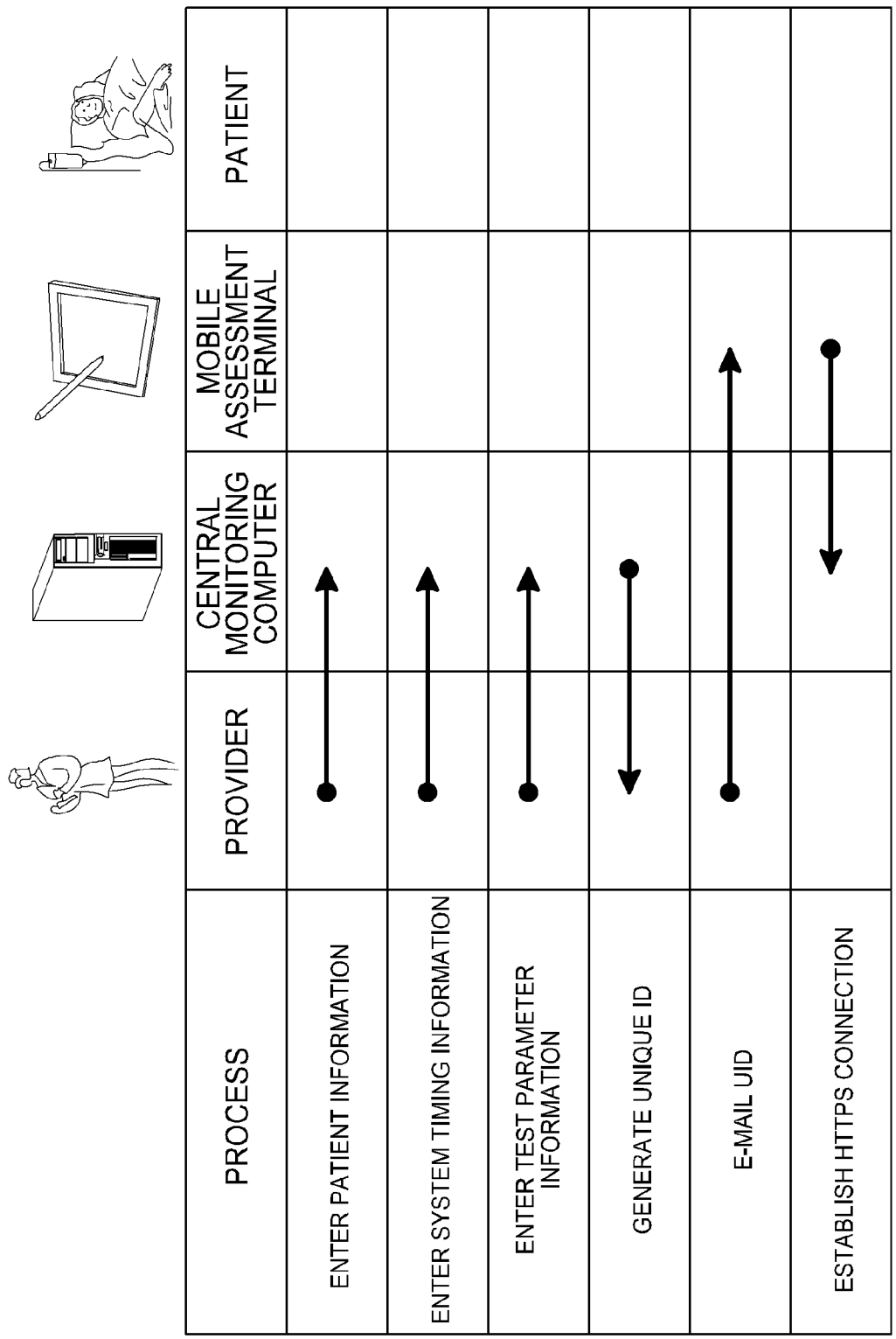

FIG. 5 is a state diagram representing a potential workflow for initializing the mobile assessment terminal, according to one implementation of the present invention.

Figure 6:
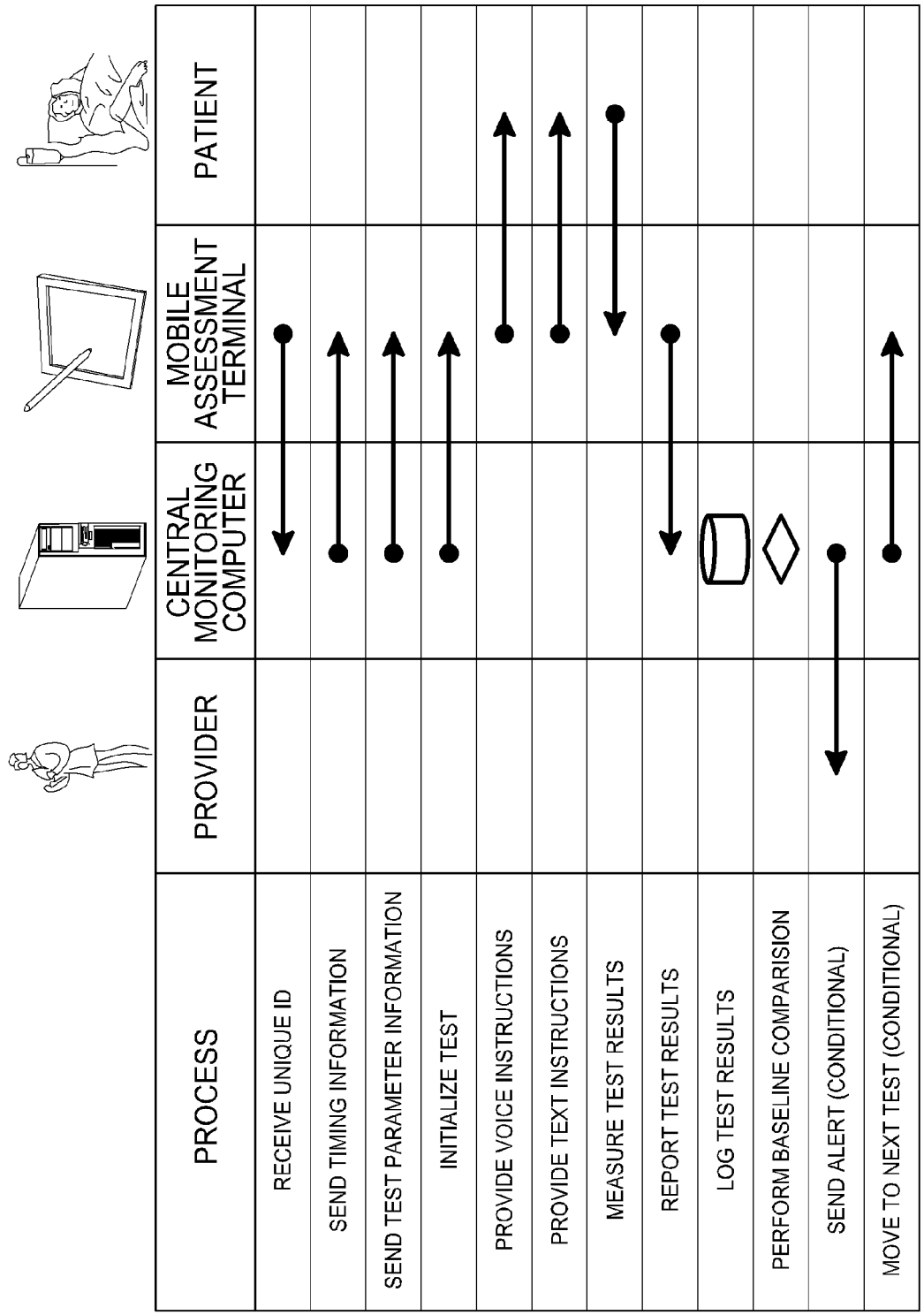

FIG. 6 is a state diagram representing a potential workflow for initializing, executing, and post processing a neurologic function test, according to one implementation of the present invention.

Figure 7:
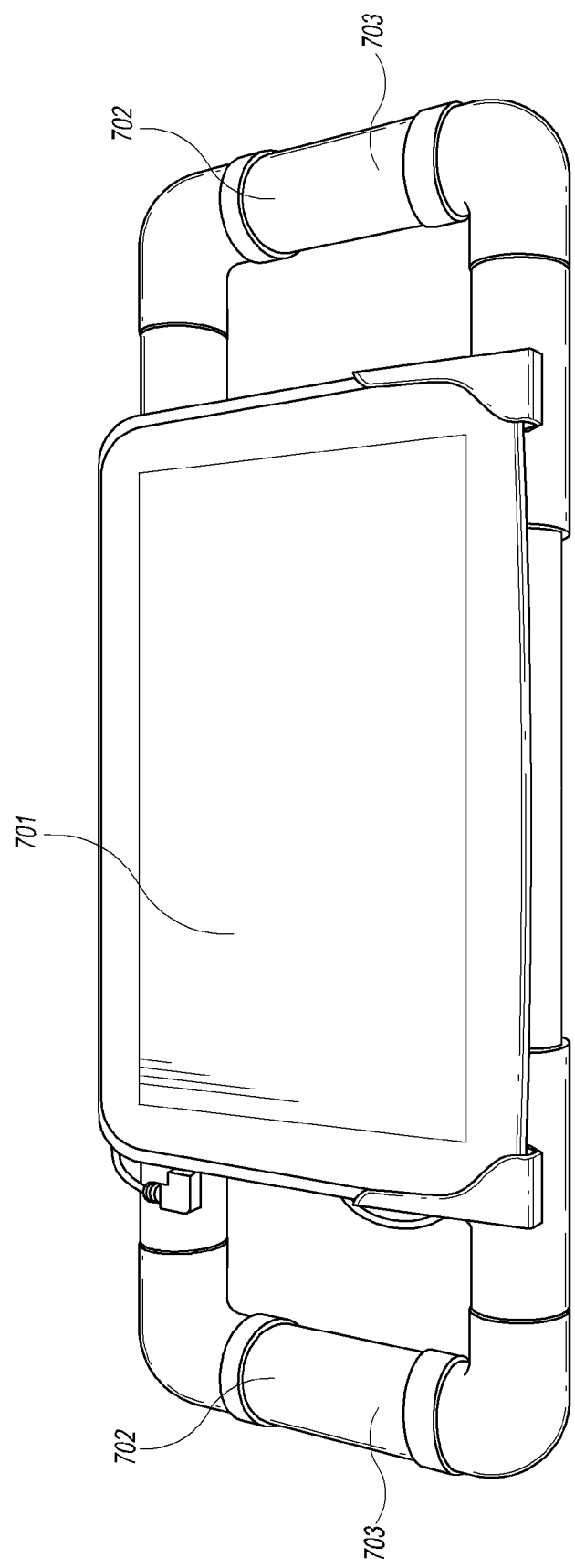

FIG. 7 is a picture of a front view of a hardware prototype representing one implementation of the present invention.

Figure 8:
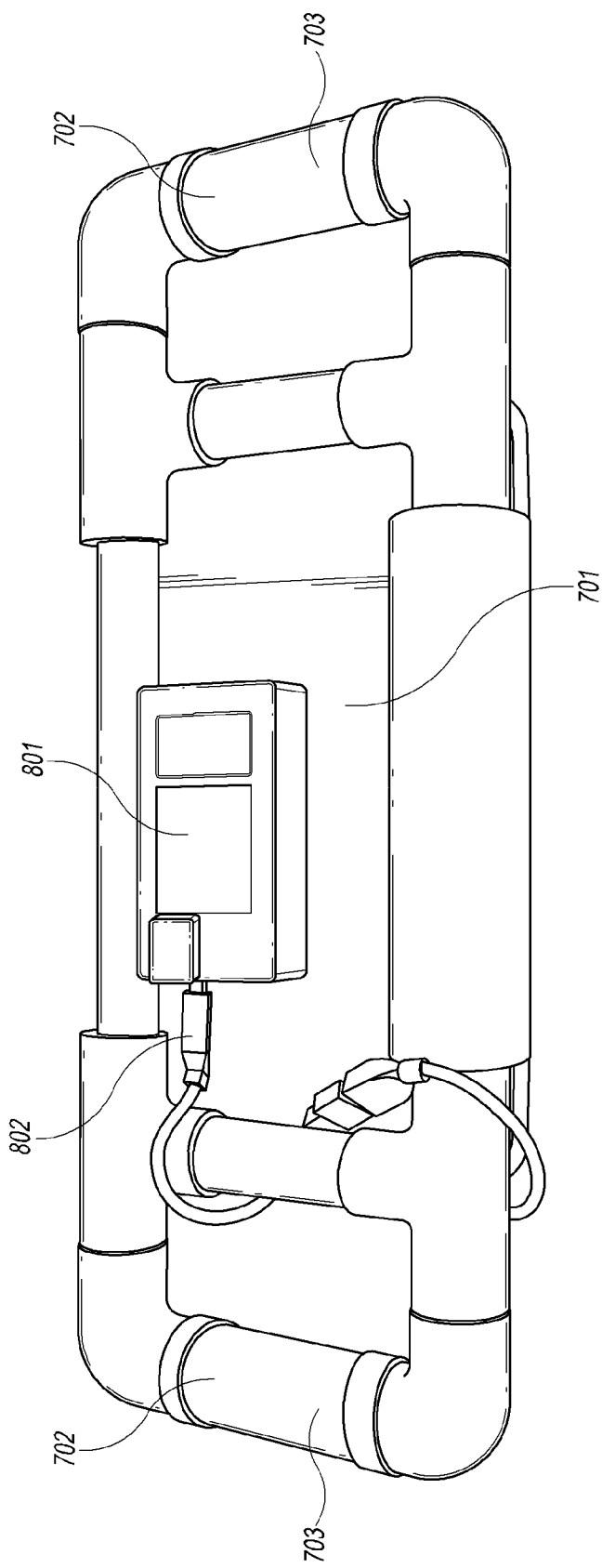

FIG. 8 is the back view of a hardware prototype representing one implementation of the present invention.

Figure 9:
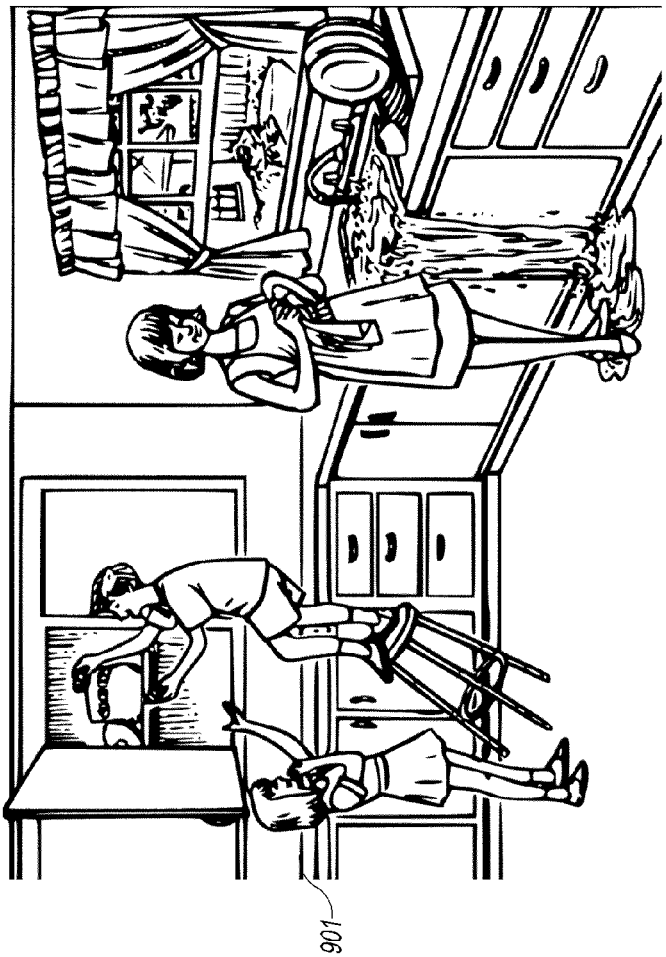

FIG. 9 is a neurologic function test that measures inattention, representing one implementation of the present invention.

Figure 10:
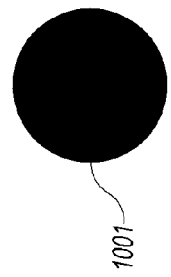

FIG. 10 is a neurologic function test that measures incoordination, representing one implementation of the present invention.

FIG. 11 is a neurologic function test that measures level of arousal representing one implementation of the present invention.

Figure 12:
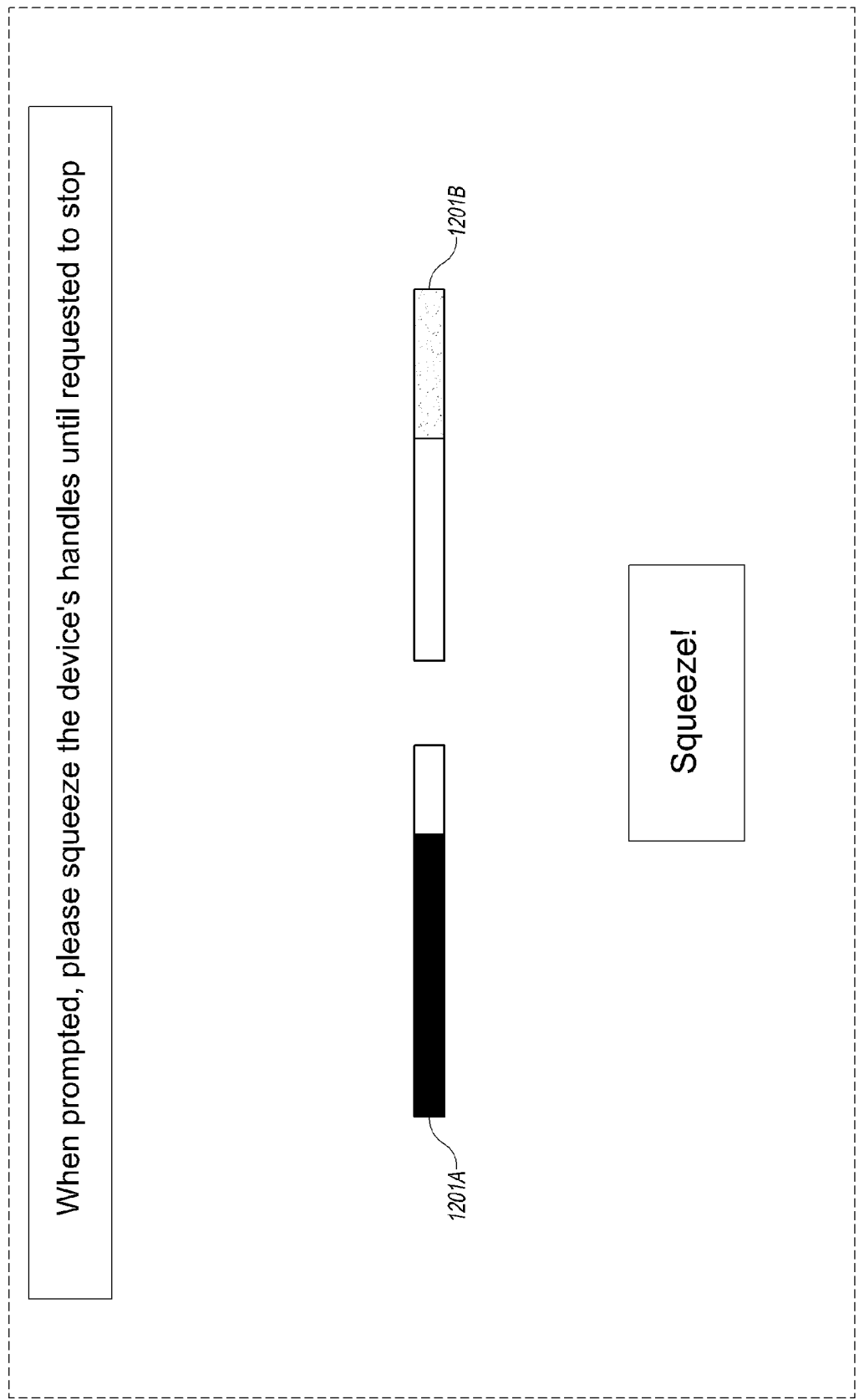

FIG. 12 is a neurologic function test that measures motor function, representing one implementation of the present invention.

FIG. 13 is a neurologic function test that measures sensory function, representing one implementation of the present invention.

Figure 14:
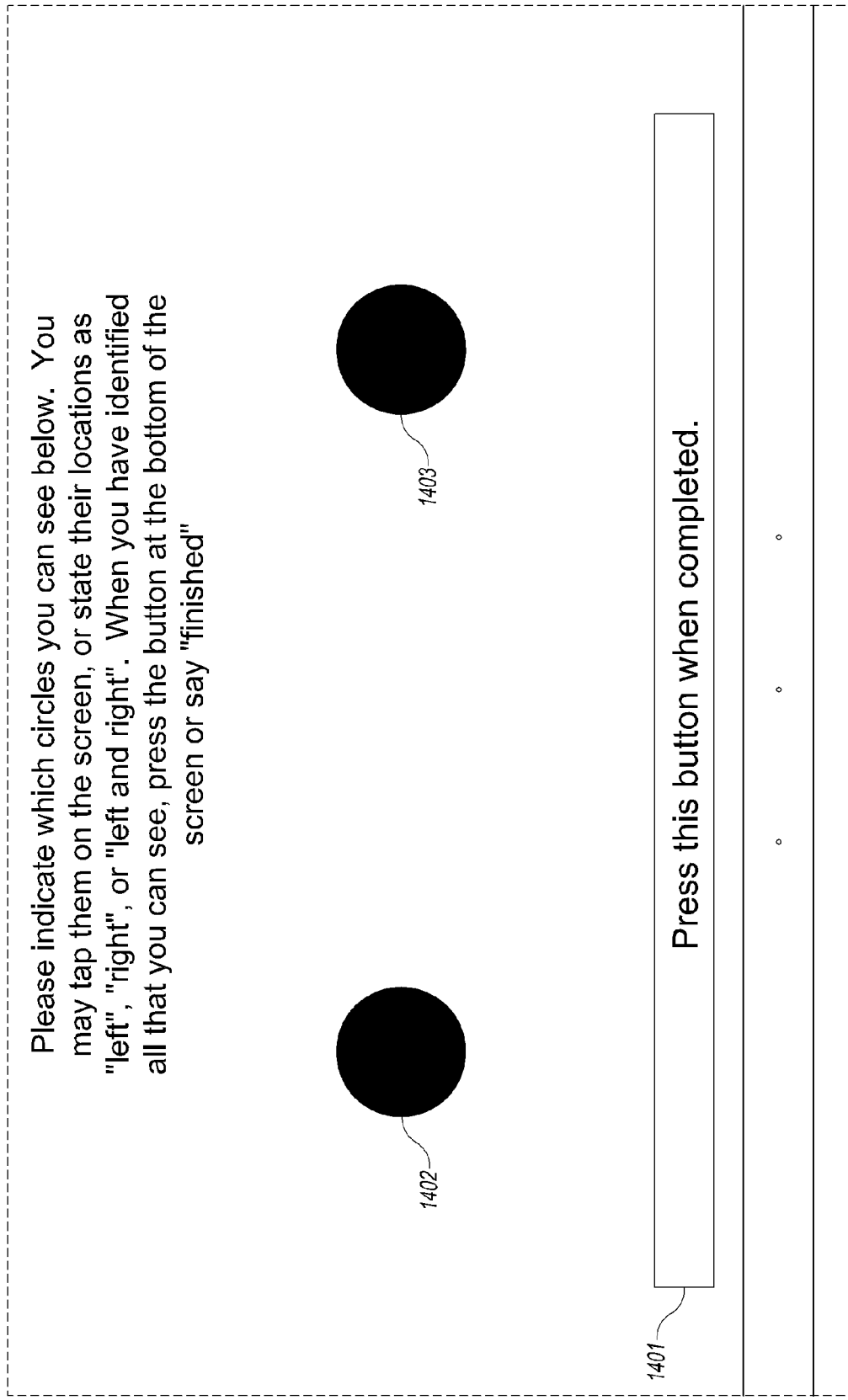

FIG. 14 is a neurologic function test that measures a visual field, representing one implementation of the present invention.

Figure 15:
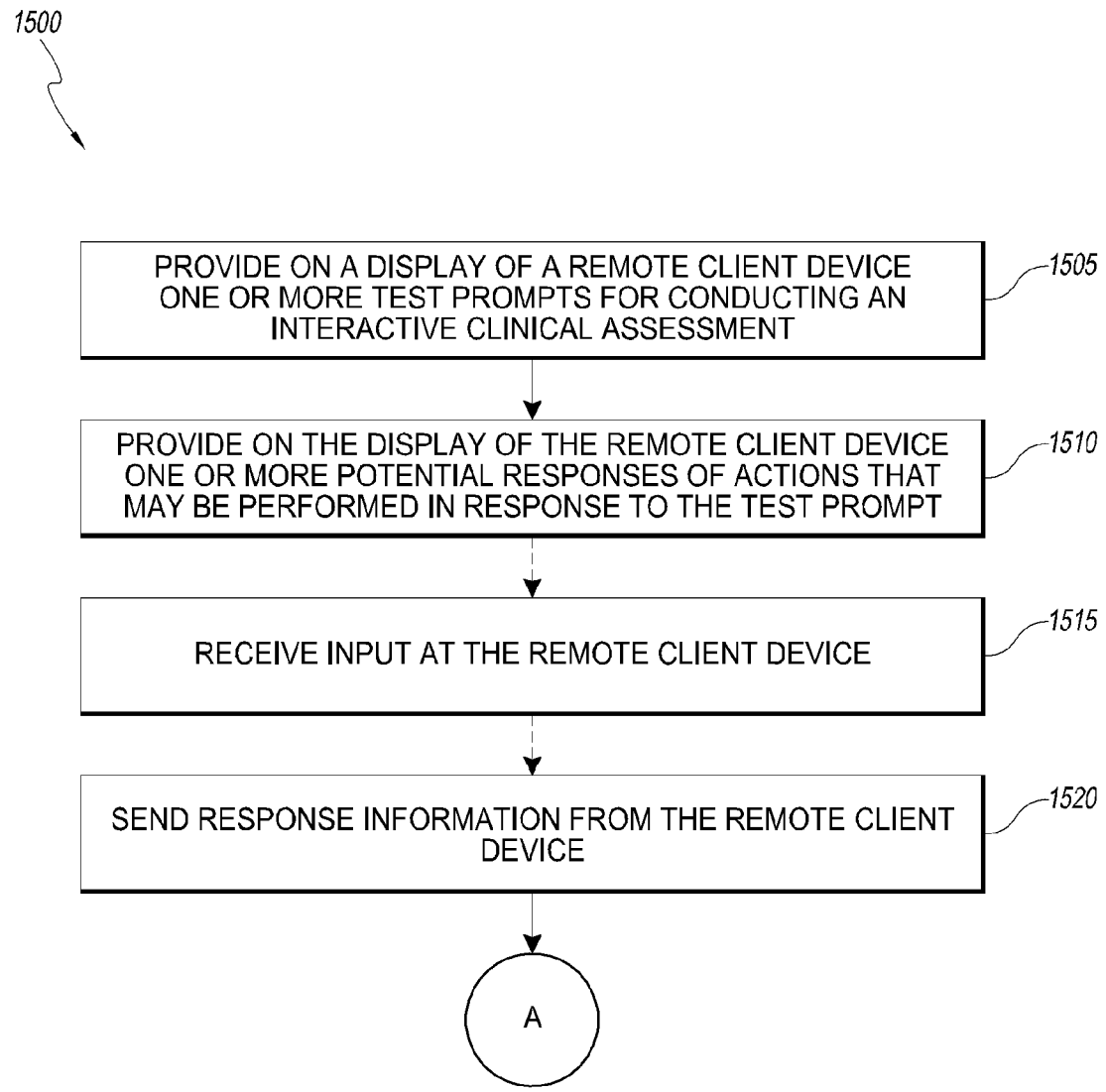

FIG. 15 is a flow diagram illustrating an exemplary process that can be implemented on the remote client device, for example, the mobile assessment terminal illustrated in FIG. 1.

Figure 16:
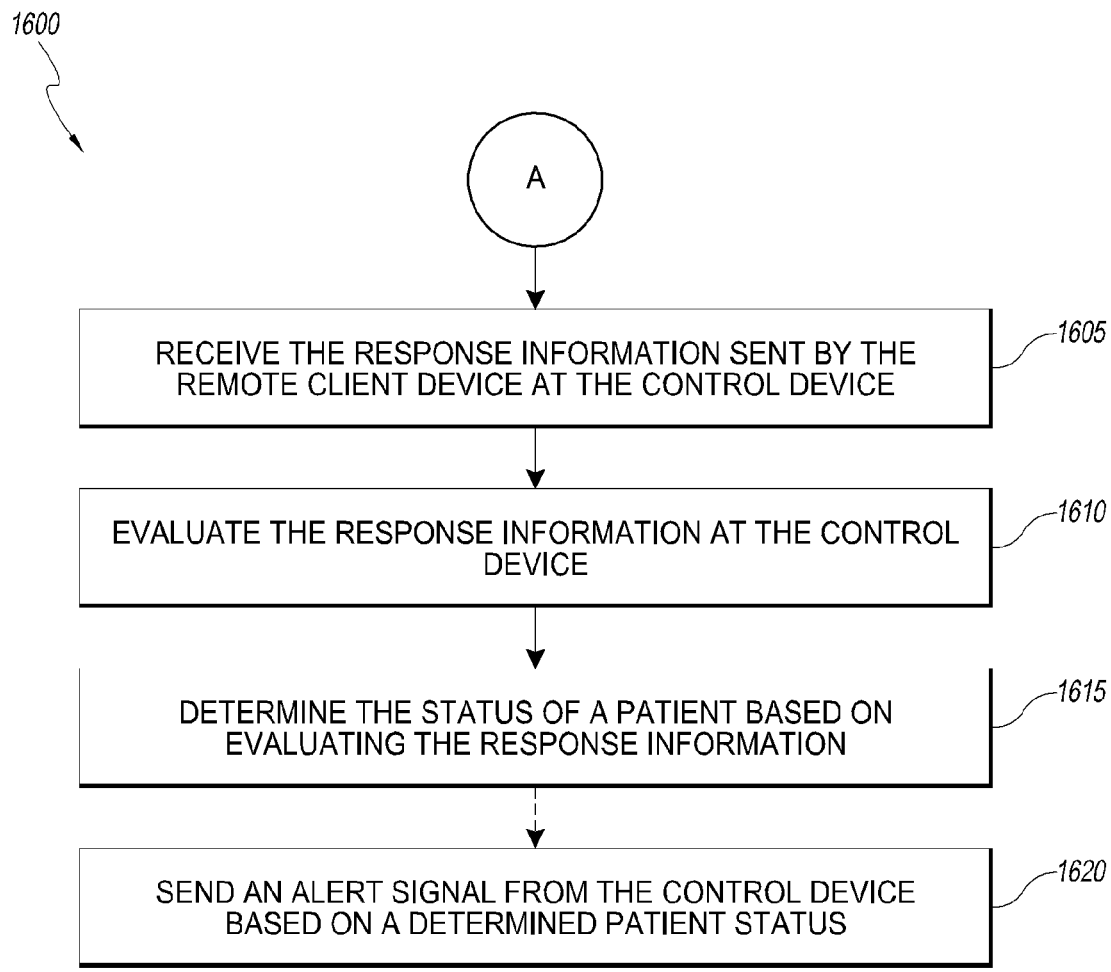

FIG. 16 is a flow diagram illustrating an exemplary process that can be implemented on a control device, for example, the central monitoring computer in FIG. 1 and FIG. 4.

Figure 17:
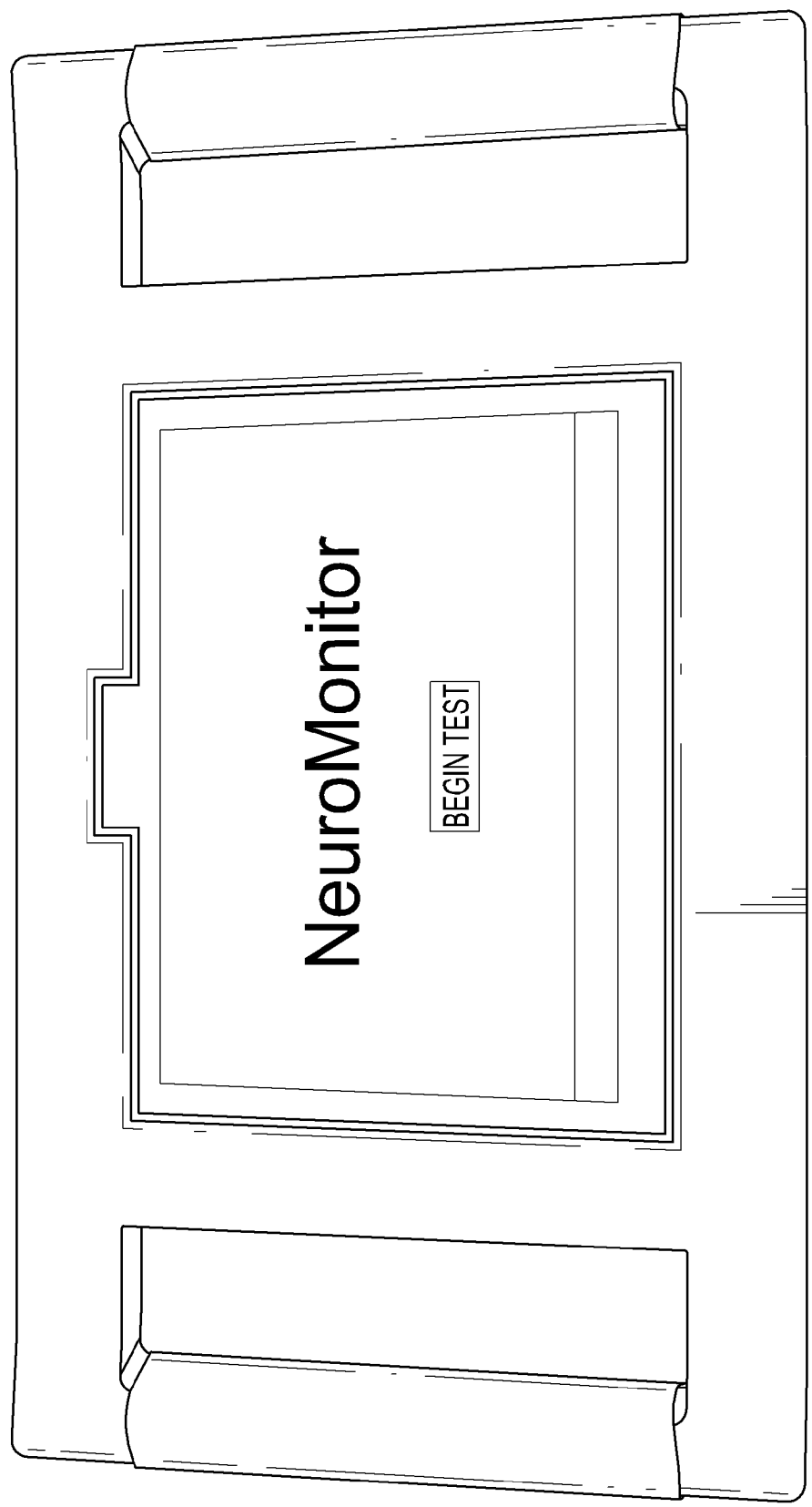

FIG. 17 is an illustration of one implementation of a client device in a housing as it may look as a finished product.

DETAILED DESCRIPTION OF CERTAIN INVENTIVE ASPECTS

Some implementations of the inventions now can be described more fully hereinafter with reference to the accompanying drawings, in which some examples of the aspects/implementations of the inventions are shown. It is to be understood that the invention implementations are not limited in its application to the details of construction, experiments, exemplary data, and/or the arrangement of the components set forth in the following description. These implementations are provided by way of example. The inventions are capable of other implementations or of being practiced or carried out in various ways. Also, it is to be understood that the terminology employed herein is for purpose of description and should not be regarded as limiting.

In the following detailed description of implementations of the disclosure, numerous specific details are set forth in order to provide a more thorough understanding of the disclosure. However, it can be apparent to one of ordinary skill in the art that the concepts within the disclosure can be practiced without these specific details. In other instances, well-known features have not been described in detail to avoid unnecessarily complicating the description. In addition, features or aspects described for one implementation may be included in other implementations as well. Like numbers refer to like elements throughout.

The clinical field of cardiology has adapted over time to utilize technology in assessing cardiac electrical functions. Many years ago, if a patient were to experience chest pain or palpitations, the only available care approach was to have a medical care practitioner (usually a medical student, intern, resident or attending) place ECG electrodes on the chest and print out an ECG report. After "running" the ECG, the care provider would utilize clinical training to interpret the electrical tracings as being normal or abnormal and then base subsequent clinical decisions on that tracing interpretation. With the advent of technology, continuous electronic ECG tracings in the form of "cardiac telemetry" became the standard. The ability for these systems to self-assess for clinically relevant abnormalities, report interpretations of the clinical data, and alarm providers when there are findings outside of pre-programmed clinical parameters, has allowed for decreased staffing by hospitals, and improved monitoring for cardiac patients throughout the world.

The field of neurologic assessments has a similar ability to monitor at least electrical physiologic parameters in the form of electroencephalography (EEG) tracings. This technology allows for care providers to place electrodes on the scalp surface and therefore record the electrical signals from within the skull cavity. These tracings are then printed and interpreted by trained neurologists or epileptology specialists. With the advent of technology, continuous electronic EEG tracings in the form of 24 hour or more continuous EEG inpatient monitoring have now become common place. Similarly, the ability for these systems to self-assess for clinically relevant abnormalities, report interpretations of the clinical data, and alarm providers when there are findings outside of pre-programmed clinical parameters, has allowed for decreased staffing by hospitals, and improved monitoring for epileptic patients throughout the world.

These examples utilize physiologic assessments of cardiac or brain function and report the results to providers in clinically meaningful ways (either as reports, summaries, or in real-time alarms if abnormalities are noted which are outside of pre-programmed clinical parameters). However, conventional technologies provide limited if any clinical assessments of patient function or clinical deficit.

Automated or semi-automated measures of assessing clinical function are lacking. The current neurologic environment has a strong need for clinical monitoring of relevant neurologic function deficit. As of now, there are approximately 800,000 acute strokes per year in the United States with stroke accounting for approximately 50% of all neurologic hospital admissions.

The clinical neurologic exam is complex, and takes a great deal of neurologic training to master. The examination overall assesses elements of thinking, cognition, memory, judgment, calculations, inattention, cranial nerve function, motor skills, sensory inputs, reflex testing, cerebellar function testing, and ambulation measurements. This complexity does not lend itself to a streamlined digital assessment or reporting. Clinical deficit scales such as the NIHSS have been developed to streamline some relevant portions of the examination (specifically for stroke patient evaluations) and have been shown to be a generally reliable exam for well-trained providers. Again, however, even this streamlined and stroke-specific examination may take 8-15 minutes for a trained care provider to perform on each individual patient in the hospital. This can result in a significant amount of time if tens or hundreds of patients need to be examined in a facility every 15 minutes or hour.

Given the above time requirements, a "bare minimum" clinical neurologic deficit examination (aka neurochecks) is generally performed during the hospitalization in lieu of a more complex/thorough neurologic examination. This is necessary to determine if there is a worsening of patient's clinical deficit since now many therapies can be administered in these types of settings, but they may be time sensitive. Rapid determination of new deficit as close to the time of onset as possible, likely correlates with outcome after such interventions. The current "standard" is for medical care providers to perform "relevant" clinical neurologic evaluations on any neurologic patient admission where the patient may have a fluctuating/worsening neurologic course while hospitalized. This assessment is currently done by clinical care providers (nurses, assistants, physicians, etc.) on an intermittent basis. There is, however, no standardized method, frequency, or level of care provider required for performing these assessments. This results in infrequent or inaccurate assessments. This poor substitute results in less than reliable and less than accurate patient deficit examinations and inherently risks patients' lives. The frequencies of assessing for neurologic deficit in the hospital range from being required every day, every shift (8 or 12 hours), or as frequently as being needed every 15 minutes throughout the entire critical care hospitalization. This frequency choice is generally left to the admitting practitioner based on severity of neurologic insult and likelihood of possible clinical worsening. Unfortunately, it is just as likely to be as affected by limitations in time, limitations of resources, and limitations on the availability of nursing staff to carry out these assessments in the hospital. Who performs these neurologic checks is often not the provider with the most expertise in neurologic care. The physicians usually admit the patient to the hospital and establish the need for these interval neurologic deficit examinations. The nursing staff are generally left to bear the burden of performing these evaluations for potentially days on end at a frequency of up to every 15 minutes. In fact, most of the time, these neurochecks are performed by nurses or medical assistants that are present in the hospital and assigned to the patient, who may not even be trained in performing reliable or accurate neurologic examinations.

To add one more level of concern and complexity to this inconsistently performed and unreliably reported clinical examination, the determination of what clinical examination techniques adequately or accurately constitute appropriate "neurochecks" has not been agreed upon either. Choices include having a nurse (a) assess change in pupil size (b) assess grip strength (c) assess arm drift (d) assess foot strength via pedal pushers (having the patient press his/her foot against resistance) (e) assess more complex neurologic deficits using either a full National Institutes' of Health Stroke Scale (NIHSS) (f) assess using a modification of the NIHSS (for example, m-NIHSS) or (g) assess using any variable combination of any of the above techniques. This lack of consistency may result in incorrect choice of clinical deficits to monitor, and may result in missing critical neurologic worsening because of this. In a perfect clinical world, a great number of these clinical assessments, such as (a) through (g) above, would be done. At the very minimum, at least the ones that are most clinically relevant to the patient's current neurologic deficit (customizable) should be able to be consistently chosen and assessed as frequently as they are truly needed, not limited by available human resources and time constraints.

Technology has now caught up with this clinical need by allowing for integrated deficit examinations using technology in a simple form factor. Mobile smartphones are often equipped with technologies which can take still camera photographs, can record sample audio recordings, and may have internal calibration and global positioning features that can assess the unit's location in space. These smartphone-like form factors currently have display screens that are combined with touch sensitive input technologies and are configured to receive input by interaction with a user through the user interface, and display information to the user by video screen output or audio output.

These small, mobile, wireless units can be configured to assess relevant neurologic clinical functions (via an interaction with the patient in numerous spheres of the neurologic examination) and report the results to providers in clinically meaningful ways (either as reports, summaries, or in real-time alarms if abnormalities are noted which are outside of pre-programmed clinical parameters). This assessment is far more reliable and reproducible in reporting the findings, than is an examination performed by either a physician or nurse. This clinical assessment method and device is not intended to assess physiologic parameters, but to assess for clinical deficit (change from baseline) in one or more basic neurologic spheres of function (level of arousal, cranial nerves, vision, motor function, sensation, speech and language, and inattention).

This Integrated Deficit Examination (IDE) method and device can be used for the majority of patients admitted to the hospital (as almost all patients have a chance of neurologic worsening while admitted to the hospital) without adding human resources or time requirements to the care provider team. This would allow for improved care throughout the world, and enable decreased hospital staffing needs and significant related costs. Certain portions of this disclosure describe examples of personal monitoring and assessment methods and devices that have a technology assembly designed to analyze both directly and indirectly entered patient data via motor control of device, tactile input, voice input, still image analysis, and responses to visual and auditory stimuli. The device itself contains one or more sensors and hardware required to assess relevant clinical neurologic parameters such as arousal, visual function, ability to follow commands, assessment of pupil size and function, facial topography, location of gaze, speech clarity, language correctness, understanding, motor positioning, motor strength, sensation, coordination and neglect. Analogous to a clinical neurologic exam assessing for differences between a baseline neurologic examination and an examination showing neurologic worsening, such devices are able to calculate the validity of stimuli responses and numerically output the presence or absence of neurologic deficit or clinical worsening compared to prior examinations or programmed standards. Reporting any change in function is done directly on the device display screen of the client device, or using CDMA or EVDO cell-phone signal (or 802.11 wireless signals) to send a report to a pager, cell-phone or central monitoring station (control device). Various examples of devices can be programmed to alert in any of these ways, if a numerical output is below a chosen threshold. The central monitoring station can track all tests and outputs. Frequency of assessments and output parameters can be changed either on the individual device or central monitoring station. In some implementations, a report can be generated by the client device or the control device, the report including test result information, for example, a list(s) of available tests, one or more graphs of the test results, and/or one or more tables with details of the tests. Such reports can be formatted to be printed. In some implementations, the report shows results for tests conducted at different times and days, for example, at various hours over a single day or over multiple days, weeks, months, or years. The client device and/or the control device can also be configured to generate reports that illustrate differences in test results, for example, comparing one test result to another test result.

FIG. 1 illustrates schematically an example of an implementation of a mobile assessment terminal (remote client device) 101 in which certain features of the present invention are implemented. Various implementations may include some or all of the described features, and/or and may include other features. The mobile assessment terminal 101 may be referred to herein as a remote client device, a mobile client device, a client device, and sometimes herein simply as a device or terminal. In some implementations, the terminal 101 is constructed as a smartphone form factor allowing for a familiar two-way interface between patient and the device. The terminal 101 is capable of wireless communication via an air interface 102 with a two-way communication component or radio communication system ("radio") 103. In other words, the radio 103 can include a transceiver configured for two-way wireless communication. For example, in various implementations, the terminal 101 can be configured to communicate via Wi-Fi, Bluetooth, CDMA, cellular, or any other wireless communication protocol and wireless network. The terminal 101 can also be capable of wired communications using conventional wire communication technology. The terminal includes a central processor 104, memory unit 105, input/output units in the form of a microphone 106, a speaker 107, an imaging circuit which may be implemented as a camera 108 (e.g., having a 14 megapixel or greater imaging system, although other image sizes greater or less than 14 megapixels) with flash capability 109 and a touch sensitive display 110. The CPU 104, memory unit 105, input/output units 106, 107, camera 108, flash 109 and display 110, as well as other elements of the terminal 101, are operationally connected to communicate and operate as needed to perform the functionality described herein. The touch sensitive display 110 includes appropriate touch sensing means, such as electronic sensing circuitry 111, configured to sense touch by way of, e.g., a pointed stylus as well as a fingertip. The circuitry 111 may be configured to sense variations in any one or more of mechanical pressure, electric resistance and spatial distribution of the touch. Three pressure sensing devices are also included to assess grip strength 112. A global positioning software/hardware unit is also included to enable assessments of position 113. An accelerometer is included to assess changes in position and velocity 114. A vibration device is included to vibrate the smartphone 115. Radio communication is realized by radio circuitry 103 and an antenna 116.

In various implementations, the means for providing on a display of a remote client device one or more test prompts for conducting an interactive clinical assessment, each displayed test prompt instructing a user to perform an action using the remote client device in response to the test prompt include the processor 104, the memory unit 105, a wireless communication component (e.g., transceiver or radio) 103 configured to communicate with a control device, and the display 114. The remote client device is configured so that the processor 104 runs a program to conduct a deficit assessment of a patient, based on information provided by the control device in communication with the remote client device Also, means for providing on the display of the remote client device one or more potential responses of actions that may be performed in response to the test prompt include the processor 104, the memory unit 105, a wireless communication component 103 configured to communicate with a control device, and the display 114. In various implementations, means for receiving a series of tests, a series of parameters and a patient profile communicated from a control device include the communication component 103, the processor 104 and the memory unit 105 operationally coupled together. In various implementations, means for receiving input from in response to displaying the one or more test prompts may include one or more of each of the following: a pressure sensor 112, a microphone, a button, a touchscreen display 110, a motion sensor (e.g., accelerometer 114), or an imaging component (e.g., camera) 108, each operationally coupled to the processor 104 and memory 105. Means for determining response information indicative of the received input may include the processor 104 and the memory unit 105, the processor 104 running a program that generates response information, that will be sent to the control device, from signals and data received from the one or more of a pressure sensor 112, a microphone, a button, a touchscreen display 110, a motion sensor (e.g., accelerometer 114), or an imaging component (e.g., camera) 108. Means for sending the response information to the control device for evaluation may include the processor 104, the memory unit 105, and the communication component or radio 116. In various implementations, means for receiving response information form the remote client device include communication components on the control device configured to receive the response information through a network. Means for evaluating the response information can include one or more processors and memory units on the control device, the one or more processors running programs that may process the response information and compare it to previous baselines for a patient, other baselines, or other desired data and identify differences and similarity. Means for determining the status of a patient based on evaluating the response information may include evaluating if the difference in the response information for a particular deficit assessment is significantly different than previous tests or a baseline, or other threshold information. Means for determining a series of tests, a series of parameters and a patient profile may include one or more processors and memory units on the control device (or in some cases the client device), the processor generating the tests, parameters based on a desired clinical assessment test or standard. Means for communicating the a series of tests, a series of parameters and the patient profile to the remote client device to conduct a deficit assessment include on the control device one or more communication components in coupled to a network and a processor.

The mobile assessment terminal 101 may be, for example, a smartphone or PDA form factor allowing for a familiar two-way interface between patient and device, and equipped with radio communication means. The method according to the present invention can in general reside in the form of software instructions, together with other software components necessary for the operation of the terminal 101, in the memory 105 of the terminal. Any type of conventional removable memory is possible, such as a diskette, a hard drive, a semi-permanent storage chip such as a flash memory card or "memory stick" etc. The software instructions of the invention may be provided into the memory 105 in a number of ways, including distribution via the network 117 from a software supplier or directly entered into the terminal 101 by the medical provider, or entered into the central monitoring computer 118 and signaled to the terminal wirelessly (note: the central monitoring computer 118 can also be referred to as a server-side control device, or as a control device). That is, the program code of the invention may also be considered as a form of transmitted signal, such as a stream of data communicated via the Internet or any other type of communication network, including cellular radio communication networks of any kind, such as CDMA 2000 etc. In the illustrated example, 4 keyboard buttons are present on the device 119 to enable direct patient entry for yes or no questions posed by the device. Other implementations may include more or less than four buttons for accepting patient input.

FIG. 2A illustrates schematically an example of an implementation of a mobile assessment terminal 201 in one form. Other configurations are also possible, and may include more or fewer of the elements listed above in FIG. 1. In the illustrated example, the form factor is developed to be approximately 5 inches wide×7 inches tall×0.75 inches in thickness in size. This is selected to be an appropriate size for most patients to be able to hold. However, in some implementations, other suitable sizes of the mobile assessment terminal may be used. As noted in FIG. 2a, the smartphone form factor is used to ensure familiarity and enable a streamlined two way communication's interface between the patient and device 201. The device 201 includes a speaker 202, microphone 203, high resolution 14 megapixel camera capable of still and video recording 204, camera flash function 205, and radio antenna 206. There is a touchscreen display 207 that is able to display user inputted text 208. A virtual keyboard (standard lettering and numbers appropriate to chosen language) 209 can be enabled or disabled on the screen for further direct user input. The device 201 also has up to 4 large keyboard buttons labeled "Yes" and "No" for further direct user input of patient responses 210. The device 201 has three handles 211 with soft grip features 212 and pressure sensors 213 embedded in the handle grips that are used to measure strength. The side handles allow for the patient to hold the device in the left hand for left sided tasks, in the right hand for right sided tasks or simply lift the device from the top if easier for the patient. Finally, there is a curved handle design 214 allowing the user to place his or her hand between the handle and device if the user has hand weakness and cannot easily hold the device when requested. If the patient has difficulty with this, in some implementations a Velcro-type strap 218 may be included on the device for the patient to place his or her arm or leg through to temporarily connect to the device 201. In some implementations, the mobile assessment terminal 201 can include a fastener, for example, a clamp, to attach the terminal 201 to a bed or another article such that it can be within easy reach of a patient or care provider personnel.

FIG. 2B illustrates schematically an example of an implementation of a mobile assessment terminal 201 in one form, with specific attention to the touchscreen interface. As noted in FIG. 2b, the smartphone form factor may be used to ensure familiarity and enable a streamlined two way communication's interface between the patient and device 201. Referring to FIGS. 2a and 2b, there is a touchscreen display that is able to display user inputted text 208, onscreen instructions 215 provided by the device 201. A virtual keyboard (standard lettering and numbers appropriate to chosen language) 209 is shown as being disabled in this figure enabling larger screen size for displayed images, text, or objects. Device generated text instructions 215 are shown as is an example of one of the visual tests (object naming 216). The device has a feature allowing the user to touch the screen in specified areas allowing this form of direct user input (touch screen) 217.

Having described both the general components and specific design in FIGS. 1 and 2A and 2B, we can now move on to describe in specific detail certain methods for obtaining these integrated deficit examinations using the device. FIG. 3, according to one implementation of the invention, illustrates a method for inputting data into an assessment terminal, for example, assessment terminals 101 and 201 (remote client devices) described above. Specific methodologies following this general model can be described thereafter. In various implementations, the assessment terminal (client device) and deficit assessment system (control device) described herein can be used to perform one or more tests or collect data for National Institutes' of Health Stroke Scale (NIHSS), modified National Institutes' of Health Stroke Scale (m-NIHSS), Alberta Provincial Stroke Strategy (APSS), FAST (face drooping, arm weakness, speech difficulty, time to call 999 or 911 (in U.S.) and the Cincinnati Pre-hospital Stroke Scale.

As illustrated in FIG. 3, the method starts at a point in time when a user interface element, in one of many forms noted below, is inputted into the terminal device 101. This method allows for sensing of the input information, processing the data via computer processor, comparing the results to chosen and programmable standards, and alarming to the provider if these findings are outside of the range of acceptable limits. The input data may be in the form of direct patient entry such as touch input 217 using the touchscreen display 207 or direct input using onscreen keyboard 209 or keyboard buttons 210. The input data may also be in the form of indirectly assessed clinical parameters obtained via device vibration 115, movement sensation 113, pressure sensors 112, still photography 108, audio recordings 106, accelerometry 114 and global position sensors 113.

Once the sensed input 301 is received via the terminal device 101, the central processor 104 can process the data via one of several mechanisms depending on the specific clinical element being assessed (this is further specified according to each clinical element below). Once processed by the CPU 302, the necessary hardware and software can compare the sensed input 301 to the pre-programmed standards 303 and can determine whether the sensed input is within range of normal. The standards can be pre-programmed or directly programmable/modifiable directly on the device 101 or central monitoring station 118. These standards can be either (a) determined from normal control data pre-entered into the device 101, (b) determined from the patient's baseline recorded examination performed with the device 101, or (c) determined from the patient's last known examination performed with the device 101.

If the sensed input 301 is within range of normal 304, this can trigger the generation of a report that can be sent to the display of the device and to the central monitoring station 305. If the sensed input 301 is not within range of normal 306, this can trigger the generation of an alarm 307 that can be sent to the display of the device and to the central monitoring station 308. In this case, the alarm can also be configured to directly page the physician on call and or the nurse caring for the patient in the hospital (the listing of which is also pre-programmed/programmable directly into the device or central station).

In some implementations, a control device or central monitoring computer 118 (FIG. 1) can receive response information from the remote client device (for example, assessment device 101 FIG. 1). The response information is indicative of input that is received at the remote client device in response to the one or more test prompts provided by the client device. The one or more test prompts can be provided on a display screen of the client device, can include an audible prompt, a visual prompt or a sensory prompt (for example, a vibration that can be perceived on the client device or a portion of the client device, which includes articles or devices attached to the client device or in communication with the client device, and thereafter may be considered part of the client device). In some implementations, the control device processes the response information to evaluate the response information, and determines the status of a patient who provided the inputs to the client device based on evaluating the response information. Evaluating the response information and determining status of a patient can include comparing the response information (indicating the responses of the patient tests) to a baseline profile for that patient. For example, a baseline generated based on previous test responses for that patient, or for similar patients, that is, a "normal" baseline for a patient. Such a "normal" baseline may be based on a plurality of patients of a similar age or that have similar health conditions.

FIG. 4 shows a typical configuration for the central monitoring computer (118) and mobile assessment terminal (101) in a network configuration. The central monitoring computer connects to a network which is connected to a router. The router interface (401) can include one or more communication modules that communicate using one or more wired or wireless communication protocols, for example, TCP/IP, 802.11, Bluetooth, and/or WiFi.

FIG. 5 shows a state diagram that describes the processes for initializing the mobile assessment terminal (101) from the central monitoring computer (118). The columns indicate major components or actors including the health care provider, the central monitoring computer (118), the mobile assessment terminal (101), and the patient. The rows indicate processing steps where the arrows indicates represents information flow from one component or actor to another component or actor. First, a health care provider inputs patient information within a web browser interface into 118. As an example, this information includes patient name, patient neurologic condition, and contact information. Second, a health care provider inputs timing information within a web browser interface into 118 that describes the time interval between neurologic function tests and the time interval between repeating all neurologic function tests. Third, the health care provider input parameter information for the neurologic function tests within a web browser interface into 118. As an example, these could include the images to be used during testing, voice recognition parameters, volume controls, and pressure sensitivities. Fourth, 118 generates an encrypted unique identifier string that is used to tie the patient information, the timing information, and the parameter information together with a mobile assessment terminal (101). This string is transferred to the mobile assessment terminal 118 electronically. In the example shown, the health care provider e-mails the string to 101. Fifth, the string is used to securely connect 101 and 118 with encrypted patient information, timing information, and test parameter information.

FIG. 6 shows a state diagram that describes the processes for executing the mobile assessment terminal (101) tests and reporting results to the central monitoring computer (118). The state diagram shown describes the execution of a single test but is not a limiting factor. In practice, multiple tests are performed on 101 and reported to 118. The columns indicate major components or actors including the health care provider, the central monitoring computer (118), the mobile assessment terminal (101), and the patient. The rows indicate processing steps where the arrows indicates represents information flow from one component or actor to another component or actor. First, the unique identifier string is used to securely connect 101 and 118 with a request to begin testing. Second, 118 responds with test parameter information to 101. Third, 118 also responds with timing information to 101. Fourth, 118 responds to initialize the test to 101. Fifth, 101 begins test with providing voice instructions and visual text instructions to the patient. Sixth, 101 measure results from the patient for the particular test. The measured results are normalized based on the individual test to a whole number. Seventh, after the time interval has been reached, as provided from 118 above, the normalized result is sent to 118. Eighth, at 118, the results are saved for historical purposes and patient trending. Ninth, as shown in FIG. 3, the results are analyzed to determine whether (a) the patient needs care and an alert is sent to the health care provider or (b) the patient can continue taking additional tests. If all tests are completed, no further action is taken.

FIG. 7 shows an example hardware device as viewed from the front of the device. 701 is an example of a computer device as depicted in 101. 702 are the handles used by the patient to hold the device in a horizontal or vertical position. 703 are embedded pressure sensors that measure the force used to hold and squeeze the handles.

FIG. 8 shows an example hardware device as viewed from the back of the device. 701 is an example of a computer device as depicted in 101. 702 are the handles used by the patient to hold the device in a horizontal or vertical position. 703 are embedded pressure sensors that measure the force used to hold and squeeze the handles. 801 is the housing for the processor used to transform the analog inputs from the pressure sensors into a digital data stream. As shown in 802, the data stream is then sent via Universal Serial Bus connection to the main terminal 701.

FIG. 9 shows an example of an "Inattention" test that is viewed on a device such as 101 or 701. In this case, the patient must select the correct number of objects from a field as shown in 901. In this case, the patient can verbally respond or select from the field indicated by 902.

FIG. 10 shows an example of an "Incoordination" test that is viewed on a device such as 101 or 701. In this case, the patient must select the yellow dot, 1001 for a specified number of trials.

FIG. 11 shows an example of a "Level of Arousal" test that is viewed on a device such as 101 or 701. In this case, the patient must hold the device at the proper angle for a specified number of seconds.

FIG. 12 shows an example of a "Motor Function" test that is viewed on a device such as 101 or 701. In this case, the patient must squeeze the pressure sensors, 703, for a specified number of seconds. The bars 1201A and 1201B visually indicate that pressure is being applied to the left and right pressure sensors, respectively.

FIG. 13 shows an example of a "Sensory Assessment" test that is viewed on a device such as 101 or 701. In this case, the patient must press the middle button, 1301, when the device 101 vibrates.

FIG. 14 shows an example of a "Visual Field" test that is viewed on a device such as 101 or 701. In this case, the patient must press each yellow dot, 1402 and 1403, and then press to end the test. Additionally, the patient can say either "Right", "Left", or "Left and Right." When the test is complete, the patient must press 1401 to complete the test.

FIG. 15 is a flow diagram illustrating a process 1500 that can be implemented on the remote client device, for example, the mobile assessment terminal illustrated in FIG. 1. Process 1500 at block 1505 provides on a display of a remote client device one or more test prompts for conducting an interactive clinical assessment. In some implementations, CPU 104 and the memory unit 105 can collectively provide on display 110 one or more test prompts for conducting the interactive clinical assessment. At block 1510, the process 1500 may provide on the display of the remote client device one or more potential responses of actions that may be performed in response to the one or more test prompts. In some implementations, CPU 104 and the memory unit 105 can collectively provide on display 110 one or more potential responses of actions that may be performed in response to the one or more test prompts. In some processes of the certain implementations, at block 1515, the client device receives input at the remote client device, the input indicative of an action performed in response to a test prompt provided on the display of the remote client device. The client device can receive such input from a camera 108 or imaging circuit, buttons on the client device (for example, buttons 210 FIG. 2), a touchscreen display (for example, touchscreen display 217 FIG. 3), a pressure sensor (for example, sensor 214 FIG. 2A), and/or a microphone (for example, microphone 106 FIG. 1, or 203 FIG. 2A), one or more motion sensors (for example, one or more of accelerometers 114 FIG. 1), or another sensor incorporated into the client device or attached to the client device and in communication with the client device. In some processes of certain implementations, at block 1520, process 1500 sends or transmits response information from the client device. This can be performed by (collectively) a processor of the client device (e.g., CPU 104) and a communication circuit of the client device (e.g., radio 103). Notation "A" indicates that in some implementations, the process can also include additional process steps as is described in reference to FIG. 16.

FIG. 16 is a flow diagram illustrating an exemplary process 1600 that can be implemented on a control device, for example, the central monitoring computer illustrated in FIG. 1 and FIG. 4. At block 1605 process 1600 receives at the control device response information that was sent by the remote client device. Such a control device (e.g., a server) can include communication equipment to receive the response information from a network (for example, network 102 and 117, FIG. 1) between the remote client device and the control device. The network connection for this and other implementations can include wired and wireless communication connections or links. At block 1610, process 1600 evaluates the response information at the control device. The control device can further include one or more processors connected to memory units, and in this implementation the one or more processors are configured to process and evaluate the response information using for example, previously collected response information (one or more test results) from the same patient, and/or test results from other patients. At block 1615, process 1600 determines the status of a patient based on evaluating the response information. This can also be performed by processors in the control device that are configured to check the processed response information against other information (e.g., a baseline) to determine if the recently received response information is different and/or significantly different. At block 1620, process 1600 sends an alert signal from the control device based on a determined patient status. The control device can be configured to send an alert signal to a pager, a telephone, a smart phone or other mobile communication device, or to a display or another computer where the alert can be visually displayed and perceived. In various implementations, the alert can be sent to a healthcare provider, the patient, and/or a caregiver of the patient, for example, a friend or relative who may be with the patient or near the patient. In some implementations, the control device sends an alert signal to the remote client device, and the patient can then call emergency services if necessary, and the remote client device can be configured to facilitate such a call by having, for example, an emergency call button to contact 911 or another emergency service. In many cases, the patient is incapacitated and cannot activate the emergency call him/herself. In some implementations, the client device is configured such that if a calculated score is less than a certain threshold for a response, or for a plurality of responses, the client device (patient side) is configured to signal either the control center, the healthcare providers (for example, programmed as either MD or nurse), or to automatically dial 911 or another programmable emergency number, and keep a connection between the client device and the number called for communication with emergency personnel.

FIG. 17 is an illustration of one implementation of a client device in a housing as it may look as a finished product. This implementation includes two handles, disposed laterally one on each side, and each handle includes a pressure sensor. The middle portion includes a touchscreen display. Such a client device can include any of the components and sensors discussed herein for testing a patient.

Having now described some aspects and features of the system, a remote client device and a control device (for example, a server-side control device) and various implementations of methods, certain specifics of the system, as related to each clinical element assessed can be described referencing mainly features illustrated in FIGS. 1, 2a, 2b and 3. The clinical examination elements to be assessed with this device and method include, but are not limited to, measuring level of arousal, visual function, the ability to follow commands, pupil size and function, facial weakness, gaze, speech clarity, language function, motor function, sensory thresholds, and inattention. Other clinical parameters of interest, using these and other technologies not listed, can also be included in the assessment program.

At the beginning of the Integrated Deficit Examination, the bedside provider or nurse can be able to interface with the device 201 to input normal ranges for each of the exam elements, or to choose from pre-entered examinations tailored to the general presentation of the patient. For example, for a patient who has a left hemisphere deficit and aphasia, or a patient with a right hemisphere deficit and neglect, or a patient with a brainstem stroke and severe lethargy or quadriplegia. This customizability can enable specific patterns of exam elements to be provided to the patient based on clinical syndrome. These examples are just a subset of the possible patterns of examination to be presented as it is likely that other neurologic disease processes (such as myasthenia gravis or guillan barre syndrome, etc.) could have similar templates developed in the future as well.

Scoring can be simplified from the more clinically complex neurologic assessments such as the NIHSS. A binary score of 0 or 1 can generally be provided based on each element to improve reliability. However, some elements may still require scoring of 0-4 to assure the ability to assess for meaningful clinical deterioration of function (such as in limb motor function). This scoring methodology assumes that a zero is normal, and increasing score is consistent with worsening clinical deficit.

The patient can be provided with this smartphone form factor device 201 and provided with a one-time instruction on using the device. Instructions can be provided by the device 201 both in audio format using the speaker 202 and in visual format using the display 215. The clinical care provider or bedside nurse can assist with the instructions and initial device interface to ensure the patient understands how to interface with the device to obtain the best clinical technology assessment. Caution can be taken to ensure that the bedside care provider does not interfere with the patient's examination, as subsequent examinations can take place without the care provider, and comparisons can likely be made between examination scores. Thereafter, the bedside provider cannot be necessary. The examination is designed to take only a few minutes to complete. After the examination is fully complete, the device 201 can process the data and report the results depending on whether scoring was within or not within the pre-programmed normal ranges.

There are eleven key clinical areas listed below that are addressed using this device and method. This listing should not be considered as full and complete as other relevant clinical features can be measured and compared using the technologies listed. These eleven elements are the core set of tests that may be included in full or in any combination for a basic assessment of clinical function. Other clinical elements may be added, and some of these listed elements may be removed and therefore should not limit the boundaries of this invention.

Level of Arousal:

In some implementations, a clinical parameter of interest is the patient's level of arousal. This is most often clinically performed by having the bedside care provider interact with the patient to determine if he or she is awake and interacting appropriately, or whether he or she is less awake (lethargic, stuporous or clinically in a coma). This clinical assessment can now be performed and analyzed using this integrated deficit examination device 101. The exemplifying method starts at a point in time when a user interface element is inputted into the terminal device 101. In this case, the input data takes the form of indirectly assessed clinical parameters obtained via device accelerometry 114 and global position sensors 113. The device can provide instructions to the patient via display 215 and/or audio signal through the speaker 202 to begin this portion of the examination. Instructions can be provided for the patient to hold the device firmly in his/her hand and lift the device from the bed to a 45 degree angle above the bed for 10 seconds. Audio countdown using the speaker 202 and video countdown using the display panel 217 can be provided to the patient, and the patient can be informed by the speaker 202 and video display 217 when this portion of the examination is over. Measurements can be made prior to the start of the examination, at the apex of the patient's lifting of the device, and again at each of the 10 seconds of the test. Other times for taking measurements are also contemplated, and may depend on the test being conducted. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to lift the device 101 for the full 10 seconds can be recorded as being fully awake and scored as a 0. If the patient lowers the device to the baseline level prior to the full 10 seconds, the score can be graded as 1. This scoring methodology assumes that a zero is normal, and increasing score is consistent with worsening clinical deficit. In another implementation of this method and device, the patient can be asked to lift the device up and down 10 times. In yet another implementation, a level of arousal can be assessed using indirectly entered data in the form of wired of wireless EEG electrodes placed on the patient's scalp. These electrodes can send signals to the client device as sensed input 301. The CPU 104 can process this sensed input 301 and compare brainwaves to either baseline or standard controls. The measurements in this case are more physiologic and would assess awake alpha rhythms (vs. slower theta or delta rhythms). The advantage of the $1^{st}$ implementation is that it can be used to assess motor function as well, thus saving time and effort during the Integrated Deficit Examination. The advantage of the $2^{nd}$ implementation is that it is a more clinically meaningful measure of arousal in that it can determine the point at which a patient is no longer able to perform the function due to somnolence. This method is not limited by the patient's baseline weakness (as some patients can lower the device to the bed due to elemental limb weakness and not due to lethargy at all). If the patient is able to perform the test at all, and at some point is no longer able to perform the test, is can be determined that the patient is not awake and interacting fully appropriately. In that case, he or she can score a 1. The advantage of the $3^{rd}$ implementation is that it is less contingent on patient cooperation as it is a direct measurement of recorded brainwave waveforms. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Eye Movements/Gaze:

In some implementations, a clinical parameter of interest is the patient's ability to move his or her eyes fully to the left and right, called gaze assessment. This is most often clinically performed by having the bedside care provider interact with the patient by asking him or her to follow the examiner's finger fully to the left and right without moving the head (eye movements only). This clinical assessment can now be performed and analyzed using this integrated deficit examination device 101. In some implementations, the exemplifying method starts at a point in time when a user interface element is inputted into the terminal device 101. In this case, the input data takes the form of clinical parameters obtained via device's camera 204 and flash 205. The device can be configured to provide instructions to the patient via display 207 and/or audio signal through the speaker 202 to begin this portion of the examination. Instructions can be provided for the patient to look forwards, to the left, and to the right. Still photographic images with camera flash 205 can be performed at each time period (forward, left, right). Audio countdown using the speaker 202 and video countdown using the display panel 207 can be provided to the patient, such that the patient can be informed by the speaker 202 and video display 207 when each portion of the examination and photograph (forward, left, right) is to be taken, and when the examination is over. Once the sensed input 301 is received via the terminal device 101, the central processor 104 can process the data and analyze relative eye positioning and symmetry compared to the other eye and medial and lateral borders of the eyelid convergences. The hardware and software can compare the sensed input 301 to the pre-programmed standards 303 and can determine whether the sensed input is within range of normal. In one implementation of this clinical assessment, the ability for the patient to look completely to one side without having one or both eyes fall short of complete gaze can be recorded as being normal and scored as a 0. If the patient has either eye incompletely looking to one side (either left or right), then score can be graded as 1. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Pupil Asymmetry:

In some implementations, a clinical parameter of interest is the presence or absence of asymmetric pupil size or function (pupil asymmetry). This is most often clinically performed by having the bedside care provider shine a flashlight into the patient's eyes, assess for pupil size change, and compare each side for asymmetry. This clinical assessment can now be performed and analyzed using this integrated deficit examination device 101. The exemplifying method starts at a point in time when a user interface element is inputted into the terminal device 101. In this case, the input data takes the form of clinical parameters obtained via device's camera 204 and flash 205. The device can provide instructions to the patient via display 207 and/or audio signal through the speaker 202 to begin this portion of the examination. Instructions can be provided for the patient to look forwards into the camera 204. Still photographic images without camera flash and with camera flash can both be performed. Audio countdown using the speaker 202 and video countdown using the display panel 207 can be provided to the patient, and the patient can be informed by the speaker 202 and video display 207 when each portion of the examination and photograph is to be taken, and when the examination is over. Once the sensed input 301 is received via the terminal device 101, the central processor 104 can process the data and analyze relative pupillary size (specifically the symmetry of the pupils compared to each other and the relative change of size of each pupil with and without light). The necessary hardware and software can compare the sensed input 301 to the pre-programmed standards 303 and can determine whether the sensed input is within range of normal. In one implementation of this clinical assessment, the ability for the patient to have both symmetrical pupil size and symmetrical change in size when light is added can be recorded as being normal and scored as a 0. If the patient has asymmetry of size (comparing left to right, or comparing the difference between size in the dark or in the light), then score can be graded as 1, This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

In some implementations, the initial input data would take the form of clinical parameters obtained via an embedded pupillometer that would use the device's camera 204 and flash 205 to assess pupil function automatically. A pupillometer is an available device, a number of which are currently on the market, that can automatically assess pupil reactivity including size, and rate of change when provided with a light source. This feature may be added to the device as well. If this technique is employed, the necessary hardware and software can compare the sensed input 301 to the pre-programmed standards 303 and can determine whether the sensed input is within range of normal. In one implementation of this clinical assessment, the normal reactivity of the pupils can be scored as 0. If the patient has asymmetry of size (comparing left to right, or comparing the difference between size in the dark or in the light) or asymmetrical rate (comparing left to right or current exam to baseline exam), then score can be graded as 1. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Visual Fields:

In some implementations, a clinical parameter of interest is the patient's ability to see using peripheral vision (left and right). This is most often clinically performed by having the bedside care provider interact with the patient to determine if he or she can count the examiner's fingers while looking forward and using only his or her peripheral vision. This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's touch-screen 217 and audio recording mechanism 203. The device can provide instructions 215 to the patient via display 217 and/or audio signal through the speaker 202 to begin this portion of the examination. The device 101 can place either one large yellow dot on a single side of the screen 217 (changing side of placement based on pre-entered clinical syndrome) or two large yellow dots (one on each side of the screen). Instructions can be provided for the patient to report whether he or she sees one large yellow dot or two large yellow dots on the screen 217. Audio instructions using the speaker 202 can be provided to the patient. In one implementation of this device 101, the patient can have the option to either touch the screen where he or she sees the large yellow dot (utilizing the touchscreen display feature of the device 217), or in another implementation of the device 101 can report verbally whether he or she sees one or two large yellow dots on the screen (utilizing the audio recording feature of the device 203). In the case of using the touchscreen, approximations as to location can suffice as this is a test determining if there are one or two large dots and not a test of accuracy regarding location of the dots. The choice as to using touch-screen 217 or audio system of voice recognition using the microphone 203 can be left to the patient given patient choice and clinical deficit. The patient can be informed by the speaker 202 and video display instructions 215 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to accurately note the presence of both large yellow dots can be recorded as having full visual fields and scored as a 0. If the patient only reports the presence of one large yellow dot when two are actually present, the score can be graded as This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Facial Asymmetry:

In some implementations, a clinical parameter of interest is the presence or absence of facial weakness (left or right). This is most often clinically performed by having the bedside care provider ask the patient to smile in order to assess for facial weakness on one side. This clinical assessment can now be performed and analyzed using this integrated deficit examination device 101. The exemplifying method starts at a point in time when a user interface element is inputted into the terminal device 101. In this case, the input data takes the form of clinical parameters obtained via device's camera 204 and flash 205. The device can provide instructions 215 to the patient via display 217 and/or audio signal through the speaker 202 to begin this portion of the examination. Instructions can be provided for the patient to look forwards and smile. Still photographic images with camera flash 205 can be collected at each time period (prior to smile and during smile). Audio countdown using the speaker 202 and video countdown using the display panel 217 can be provided to the patient, and the patient can be informed by the speaker 202 and video display 217 when each portion of the examination and photograph is to be taken, and when the examination is over. Once the sensed input 301 is received via the terminal device 101, the central processor 104 can process the data and analyze relative facial topography (specifically the symmetry of the nasio-labial fold). The necessary hardware and software can compare the sensed input 301 to the pre-programmed standards 303 and can determine whether the sensed input is within range of normal. In one implementation of this clinical assessment, the ability for the patient to have a symmetrical smile and equivalent/symmetrical nasio-labial fold creases on each side can be recorded as being normal and scored as a 0. If the patient has asymmetry noted, then score can be graded as 1. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Motor Functioning:

In some implementations, a clinical parameter of interest is the patient's strength in his or her arms and legs. This is most often clinically performed by having the bedside care provider interact with the patient to assess arm and leg strength by having the patient hold up the arm or leg for a predetermined amount of time and assess for downward drifting of the limb. This clinical assessment can now be performed and analyzed using this integrated deficit examination client device 101. The exemplifying method starts at a point in time when a user interface element is inputted into the terminal device 101. In one implementation of the device, the input data takes the form of indirectly assessed clinical parameters obtained via device accelerometry 114 and global position sensors 113. The device can provide instructions 215 to the patient via display 217 and/or audio signal through the speaker 202 to begin this portion of the examination. Instructions can be provided for the patient to hold the device firmly in his/her hand and lift the device from the bed to a 45 degree angle above the bed for certain time periods, for example, 10 seconds, for an assessment using an arm or 5 seconds for an assessment using a leg. Such time periods are examples, other time periods for an assessment using an arm and/or leg can also be used. In another implementation, the client device can include an imaging circuit including an imaging device, and an image analysis program, and the device collect images of a person holding up their arm or leg without any weight bearing for a certain amount of time, and the image analysis program can determine response information based on the collected images. Audio countdown using the speaker 202 and video countdown using the display panel 217 can be provided to the patient, and the patient can be informed by the speaker 202 and video display 217 when this portion of the examination is over. Measurements can be made prior to the start of the examination, at the apex of the patient's lifting of the device, and again at each of the 5-10 seconds of the test. Patients can be tested both on the right side and the left side. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to lift the device 101 for the full 5-10 seconds without change in downward positioning of the device can be recorded as having normal strength and scored as a 0. If the patient lowers the device less than 50% of the distance to the bed (determined mathematically by the device by comparing initial position to apex position and dividing by 2) prior to the full 5-10 seconds, the score can be graded as 1. If the patient lowers the device more than 50% of the distance to the bed (determined mathematically by the device by comparing initial position to apex position and dividing by 2) prior to the full 5-10 seconds, the score can be graded as 2. If the patient lowers the device to the baseline level prior to the full 5-10 seconds, the score can be graded as 3. If there is no change of position or acceleration noted, the score can be graded as 4. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well. In many cases, the motor strength exam of the leg can be excluded to optimize simplicity and timing of exam, but in the less likely case where leg strength is a clinically relevant measurement (such as in anterior cerebral artery strokes or internal capsule strokes), this option can be included.

In some implementations, the input data takes the form of directly assessed clinical parameters obtained via device pressure sensors 112 to measure grip strength bilaterally. The device can provide instructions 215 to the patient via display 217 and/or audio signal through the speaker 202 to begin this portion of the examination. Instructions can be provided for the patient to hold the device firmly in his/her hand and squeeze the handle as hard as possible. Audio countdown using the speaker 202 and video countdown using the display panel 217 can be provided to the patient, and the patient can be informed by the speaker 202 and video display 217 when this portion of the examination is over. Measurements can be made prior to the start of the examination, and of the highest value of the pressure monitor during the test. Patients can be tested both on the right side and the left side for hand grip strength. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, if the highest pressure sensed is within a pre-programmed range of standard normal values, the patient can be recorded as having normal strength and scored as a 0. If the patient's grip strength is lower than 75% of normal, the patient can be scored as 1. If the patient's grip strength is lower than 50% of normal, the patient can be scored as 2. If the patient's grip strength is lower than 25% of normal, the patient can be scored as 3. If there is no change in grip strength noted, the score can be graded as 4. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Incoordination:

In some implementations, a clinical parameter of interest is the patient's ability to coordinate fine movements. This is most often clinically performed by having the bedside care provider interact with the patient by having him or her touch the tip of an object with his or her finger and then touch his or her own nose. This is a clinical measure of coordination of that limb. This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's touch-screen 217. The device can provide instructions 215 to the patient via display 217 and/or audio signal through the speaker 202 to begin this portion of the examination. The device 101 can place one large yellow dot on a single side of the screen 217 (changing side of placement based on pre-entered clinical syndrome). Instructions can be provided for the patient to touch the large yellow dot with his or her fingertip 10 times. Audio instructions using the speaker 202 can be provided to the patient. Approximations as to location cannot suffice in this case (different from the assessment of visual fields) as this is a test of repetition and accuracy. The patient can be informed by the speaker 202 and video display 217 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. Percentage of accuracy can be determined mathematically by the device by calculating the distance between yellow dot and touch of the screen. For the total trials, total distance divided by total trials can yield an average distance for bulls-eye target and can be used as a quantifiable surrogate for incoordination. In one implementation of this clinical assessment, the ability for the patient to accurately touch the one large yellow dot can be recorded as having normal coordination and scored as a 0. If the patient's average distance is lower than 75% of the standard values programmed, the patient can be scored as 1 for that limb. The final determined score for this element can then be compared to the standards 303 that have been pre-programmed or directly programmable/modifiable directly on the device 101 or central monitoring station 118 (as described above). For this incoordination assessment, the score for the previously assessed motor exam can be used to compare whether incoordination is more than would be expected for the level of weakness. For example, if the patient scored a normal 0 for the prior motor test, then 75% can be used as the threshold for scoring a 1 on this incoordination assessment. However, if the patient scored a 1 for the motor test, then perhaps 50% can be used as the threshold for scoring a 1 on this incoordination assessment. Exact thresholds can be programmed and programmable into the devices. In most cases, it is likely that the patient's baseline examination can be used as a comparator as well. In many cases, the coordination of the leg can be excluded to optimize simplicity and timing of exam, but in the less likely case where leg coordination is a clinically relevant measurement (such as in cerebellar strokes), this option can be included.

Sensory Assessment:

In some implementations, a clinical parameter of interest is the patient's ability to accurately sense when he or she is being touched on one of his or her limbs. This is most often clinically performed by having the bedside care provider interact with the patient to determine if he or she can feel a touch sensation on each arm and leg. This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's touch-screen 217 and audio recording mechanism 203. The device can provide instructions to the patient via display 217 and/or audio signal through the speaker 202 to begin this portion of the examination. The device 101 can utilize a vibration feature 115 to vibrate the smartphone form factor during this test. Instructions can be provided for the patient to report whether he or she feels the vibration of the device 101 when it is in his or her left hand and then right hand. He or she can be asked whether (a) it can be felt at all and (b) it feels normal. Audio instructions using the speaker 202 can be provided to the patient. In one implementation of this device 101, the patient can have the option to either touch the large "Yes" "No" buttons 210 to answer the questions, or in another implementation of the device 101 can report verbally the answers to these two questions. The choice as to using keyboard buttons 210 or audio system of voice recognition using the microphone 203 can be left to the patient given patient choice and clinical deficit. The patient can be informed by the speaker 202 and video display 217 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to accurately note the presence of the vibration as being normal can be recorded as having normal sensation and scored as a 0. If the patient reports the sensation as being present but not normal vibration, then the score can be graded as 1. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Speech Clarity Assessment (Dysarthria):

In some implementations, a clinical parameter of interest is the patient's ability to speak clearly. This is most often clinically performed by having the bedside care provider interact with the patient to determine if he or she can speak without slurring his or her words (assessing for clinical dysarthria deficit). This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's audio recording mechanism 203. The device can provide instructions to the patient via display 217 and/or audio signal through the speaker 202 to begin this portion of the examination. The device 101 can utilize a speaker 202 and display screen 217 for providing instructions 215 to the patient. Instructions can be provided asking the patient to repeat a standard sentence such as "The President Lives in Washington" or "A Blue Sky in California". The patient can be informed by the speaker 202 and video display 217 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to clearly repeat a standard sentence can be recorded as having normal speech clarity and scored as a 0. If the patient's speech sample is clear (defined as the computer accurately recognizing 4-5/5 words for "The President Lives in Washington" or "A Blue Sky in California", then the score can be graded as 0. If the computer accurately recognizes 0-3/5 words, then the score can be graded as 1. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Language Deficit (Aphasia):

In some implementations, a clinical parameter of interest is the patient's ability to produce and understand language. This is most often clinically performed by having the bedside care provider interact with the patient to determine if he or she can name objects on a page (such as key, glove, cactus, feather or hammock), repeat words, and read sentences. This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's touch-screen 217 and audio recording mechanism 203. The device can provide instructions to the patient via display 217 and/or audio signal through the speaker 202 to begin this portion of the examination. The device 101 can first place a picture of 5 standard objects (listed above) on the display screen 217 (changing side of placement based on pre-entered clinical syndrome). Instructions can be provided for the patient to report the name of each object when highlighted or touch the object named by the device. Audio instructions using the speaker 202 can be provided to the patient. Speech clarity is not assessed in this portion of the examination as this is a measure of understanding and language, not speech clarity. However, errors in phonemic substitutions or incorrect words can be assessed in this portion of the examination. English can be the language used in one example, but other languages Including Spanish can be options for the device. In one implementation of this device 101, the patient can have the option to either touch the screen where he or she sees the requested object (utilizing the touchscreen display feature of the device 217) or can report verbally the name of the object highlighted on the screen (utilizing the audio recording feature of the device 203). Both options can be used in order to measure understanding. In another implementation of this device the patient can report verbally the name of the object highlighted on the screen (utilizing the audio recording feature of the device 203). This option can be provided to measure language output. The patient can be informed by the speaker 202 and video display 217 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment (understanding), the ability for the patient to accurately touch or verbally report the correct object's location or name can be recorded as having normal comprehension and scored as a 0. If the patient correctly notes by touch or verbal report <75% of the objects, the score can be graded as 1. If the patient correctly notes by touch or verbal report <50% of the objects, the score can be graded as 2. This scoring methodology assumes that a zero is normal, and increasing score is consistent with worsening clinical deficit. In another implementation of this clinical assessment (language output), the ability for the patient to accurately report the correct object's name verbally and without phonemic substitutions or incorrect word choices can be recorded as having normal language output and scored as a 0. If the patient correctly reports <75% of the objects, the score can be graded as 1. If the patient correctly notes <50% of the objects, the score can be graded as 2. This scoring methodology assumes that a zero is normal, and increasing score is consistent with worsening clinical deficit. The final determined score for this element can then be compared to the standards 303 that have been pre-programmed or directly programmable/modifiable directly on the device 101 or central monitoring station 118 (as described above). In most cases, it is likely that the patient's baseline examination can be used as a comparator as well.

Inattention/Neglect Assessments:

In some implementations, a clinical parameter of interest is the patient's ability to attend to both sides of his or her environment using multiple sensory modalities (such as touch or vision). This is most often clinically performed by having the bedside care provider interact with the patient to determine if he or she can feel bilateral sensations on each arm when given simultaneously or can see both sides of a visual image. This clinical assessment can now be performed and analyzed using this integrated deficit examination device 101. The exemplifying method starts at a point in time when a user interface element is inputted into the terminal device 101. In this case, the input data takes the form of directly assessed clinical parameters obtained via the device's touch-screen 217 and audio recording mechanism 203. The device can provide instructions to the patient via display 217 and/or audio signal through the speaker 202 to begin this portion of the examination. The device 101 can place a standard image on the display screen (one of a woman washing dishes while a boy and girl try to get cookies from a cookie jar). Instructions can be provided for the patient to report whether he or she sees one, two or three persons in the image. Audio instructions using the speaker 202 can be provided to the patient. In one implementation of this device 101, the patient can report verbally whether he or she sees one, two or three persons in the image on the screen (using the audio recording feature of the device 203). The patient can be informed by the speaker 202 and video display 217 when this portion of the examination is over. Once the sensed input 301 is received via the terminal device 101, the central processor 104 can process the data. The necessary hardware and software can compare the sensed input 301 to the pre-programmed standards 303 and can determine whether the sensed input is within range of normal. In one implementation of this clinical assessment, the ability for the patient to accurately note the presence of 3 persons in the image can be recorded as having no evidence of neglect and scored as a 0. If the patient reports 2 persons in the image, the score can be graded as 1. If the patient reports 1 or 0 persons in the image, the score can be graded as 2. This scoring methodology assumes that a zero is normal, and increasing score is consistent with worsening clinical deficit. For this assessment, the score for the previously assessed visual field exam can be used to modify the neglect score on this test (for example, if the patient scored a normal 0 for the prior visual field test, then the scoring scheme above can be used. If the patient scored a 1 on the visual field test, and scores a 2 on this neglect test, he or she can arbitrarily only be given a 1 on this test instead of the full abnormal score of 2). Exact thresholds can be programmed and programmable into the device). The final determined score for this element can be compared to the standards 303 that have been pre-programmed or directly programmable/modifiable directly on the device 101 or central monitoring station 118 (as described above). In most cases, it is likely that the patient's baseline examination can be used as a comparator as well.

Upon completion of one, more than one, all, or any combination of these examination elements, or a procedure that includes additional examination elements, the totals can be tallied electronically for reporting of results of this integrated deficit examination. Since each element reports a numerical value (usually binary 0 or 1), a total score can be developed and compared to standard normals, to pre-programmed values chosen by the care provider, and prior examinations of the same patient. Similarly, each element can be compared to standard normal, to pre-programmed values chosen by the care provider, or prior exam scores of the same patient. If the overall sensed input totals 301 are within range of normal, this can trigger the generation of a report that can be sent to the display of the device 207 and to the central monitoring station 118. If an individual sensed input 301 is not within range of normal, this can trigger the generation of an alarm that can be sent to the display of the device 207 and to the central monitoring station 118. In this case, the alarm can also be configured to directly page the physician on call (the listing of which is also pre-programmed/programmable directly into the device 101 or central control station 118).

Additionally, certain specific issues of features, programming, customizability are described below.

A remote client device (for example, mobile assessment terminal 101) can be designed to have both a direct user interface and ability to be programmed at the central monitoring station 118 (for example, control device such as a server-side control device). The client device's direct user interface can include a touch-screen display 207, virtual keyboard 209, and keyboard buttons 210. This can enable the care provider to interface with the device 101 and CPU 104 directly to choose from various patterns of examinations. Examples of examinations include, but are not limited to, classic examinations tailored for left hemisphere stroke patients, right hemisphere stroke patients, posterior circulation stroke patients, brainstem stroke patients, patients with syndromes of visual deficit, or patient's that have baseline problems with auditory function. The provider can enable the function for use in his or her particular patient by choosing from a standard pick-list on the display 207 or entering in custom exam elements he or she wishes to monitor. Thus, this device can be used in variable settings where the provider wishes to monitor an entire neurologic exam, or where the provider simply wishes to assess when or if one element has neurologic worsening (such as weakness of an arm only).

A further feature of this client device 101 includes the ability for the provider to customize the program to alert him or her for different degrees of worsened deficit. For example, the provider may only wish to be notified if the patient's strength decreases by more than 50%, or if the patient's level of arousal decreases by more than 25%. The device can be programmed to alarm if findings are outside of the programmed parameters (for individual items or total score). This alarm feature can be programmed to alert the care provider by signaling the central monitoring station 118 (control device) or the client device 101 can be programmed to directly page or text the provider on call (or nurse caring for the patient) assuming the provider programs in the correct pager or cell-phone number. This option is possible since the client device itself 101 may have wireless cell-phone technology included. In some implementations, the client device and/or the control device that the client device communicates with can provide an alert (for example, to a caregiver, medical personnel, or anyone else or to any facility) if the patient has not performed some action with the client device, for example, if the patient has not taken a test using the device, if the patient has not activated the client device, or if the patient began a series of tests but did not finish the tests.

A further feature is specific to two way communication regarding the alarm signal. In some implementations where a client device 101 is configured and programmed to do so, once the care provider or nurse is signaled by pager or cell-phone that there may be a worsening of clinical neurologic deficit, the client device itself 101 can act as a telephone and enable a return call to enable the nurse or doctor to communicate directly with the patient (to see if there is a true neurologic worsening or if the patient did not fully cooperate with the exam for other reasons). A video-camera feature incorporated in the client device can allow this return call to take place by both audio and video methods (cell-phone to cell-phone). This option is possible in implementations of the client device 101 that have wireless cell-phone technology and video camera features included.

The device 101 is developed to communicate wirelessly to the control station 118.

The device 101 has been developed to have two sets of "Yes" "No" buttons located in each visual field in order to allow its use for both patients with visual field deficits and neglect syndromes.

The device 101 is configurable for numerous languages including, but not limited to, English and Spanish. These languages can be programmed into the device and can be programmed by the care provider to change the virtual keyboard, audio instructions, and display text to the most appropriate language for the patient.

The device 101 is configurable for how frequent the provider wishes to assess the patient's level of functions. This can be modified to assess the patient as frequently as every 15 minutes to as infrequently as every day or even every other day.

The various illustrative methods, logical blocks, modules, circuits and algorithm steps described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and steps described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some implementations, particular steps and methods may be performed by circuitry that is specific to a given function.

In one or more aspects, the functions and processes described may be implemented in hardware, digital electronic circuitry, computer software, firmware, including the structures disclosed in this specification and their structural equivalents thereof, or in any combination thereof. Implementations of the subject matter described in this specification also can be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium. The steps of a method, algorithm or manufacturing process disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blue-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. To the extent that the word "exemplary" is used herein, it exclusively means "serving as an example, instance, or illustration." Any implementation described herein as "exemplary" is not necessarily to be construed as preferred or advantageous over other possibilities or implementations. Additionally, a person having ordinary skill in the art will readily appreciate, the any relative term used or indicated herein, for example, "upper" and "lower," are sometimes used for ease of describing the figures, and indicate relative positions corresponding to the orientation of the figure on a properly oriented page, and may not reflect the proper orientation of an IMOD as implemented.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, a person having ordinary skill in the art will readily recognize that such operations need not be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

What is claimed is:

1. A method of obtaining interactive clinical assessment data using a remote client device, the method comprising:
providing by a handheld remote client device a plurality of test prompts for conducting an interactive clinical assessment, each test prompt instructing a patient to perform an action using the client device, the client device comprising a processor, a display, at least one handle mechanically integrated with the client device, a circuit configured to produce a vibration test prompt on the at least one handle, and a plurality of sensors integrated in the client device;
receiving information from the plurality of sensors indicative of a user input response to the test prompts, the information including
data indicative of movement of the client device,
image data capturing the position of the patient's eyes,
image data capturing the pupils of eyes of the patient,
touch data indicative of the patient's peripheral vision,
image data capturing the patient's face,
grip pressure data, touch data selecting a displayed target,
audio data or touch data responsive to the vibration test prompt,
audio data indicative of clarity of speech,
audio data or touch data input data representing identifying objects provided on the display, and
audio data or touch data indicative of the number of objects provided on the display; and
generating, by the processor, response information indicative of the information received from the plurality of sensors.

2. The method of claim 1, further comprising sending, by the client device, the generated response information over a communications network.

3. The method of claim 1, wherein the client device further comprises a pressure sensor disposed on the at least one handle of the client device for sensing hand grip pressure, a movement sensor for sensing horizontal and vertical motion of the client device, a microphone and voice recognition system for receiving an audio input, a camera positioned to generate an image of an area in front of the display, and a touchscreen for sensing a touch data input at the display.

4. The method of claim 2, wherein the data indicative of movement of the client device is received from the movement sensor, the image data is received from by the camera, the grip pressure data is received from the pressure sensor, the touch data is received from the touchscreen, and the audio data received from the microphone and voice recognition circuit.

5. The method of claim 1, wherein providing a plurality of test prompts comprises providing visual test prompts on a display of the client device.

6. The method of claim 1, wherein providing a plurality of test prompts comprises providing audio test prompts using a speaker of the client device.

7. The method of claim 1, further comprising receiving clinical tests at the remote device, and wherein the plurality of test prompts are based at least in part on the received clinical tests.

8. The method of claim 1, further comprising receiving clinical test parameters at the remote client device, and wherein the plurality of test prompts are based at least in part on the received test parameters.

9. The method of claim 1, further comprising receiving patient information at the remote client device, and wherein the plurality of test prompts are based at least in part on the received patient information.

10. The method of claim 1, further comprising:
receiving the response information sent by the remote client device at a control device,
evaluating at the control device the response information, and
determining the status of the patient based on evaluating the response information.

11. The method of claim 10, further comprising sending an alert signal from the control device based on a determined patient status.

12. The method of claim 1, further comprising sending clinical tests, test parameters, and patient information from a control device to the remote client device, wherein the plurality of test prompts and one or more potential responses of actions that may be performed in response to the plurality of test prompts are at least partly based on the based clinical tests, test parameters, or patient information.

13. The method of claim 1, further comprising evaluating the response information to determine a change from baseline results of a particular patient.

14. The method of claim 1, further comprising:
receiving a series of tests, a series of parameters and a patient profile for responses at the remote client device,
determining response information indicative of responses received at the remote client device;
transmitting the response information to the control device; and
evaluating the response information at the control device to determine a clinical status of the patient.

15. The method of claim 14, further comprising sending, by a client device, the response information over a communications network.

16. The method of claim 1, further comprising receiving EEG data at the client device while providing a test prompt for the patient to move the client device.

17. The method of claim 1, further comprising providing a test prompt for the patient to move eyes fully to the left or right while receiving image data capturing the position of the patient's eyes.

18. The method of claim 1, further comprising providing a test prompt for the patient to grip the at least one handle of the client device while receiving the grip pressure data.

19. A method of obtaining interactive clinical assessment data using a remote client device, the method comprising:
providing by a handheld remote client device a plurality of test prompts for conducting an interactive clinical assessment, each test prompt instructing a patient to perform an action using the client device, the client device comprising a processor, a display, at least one handle mechanically integrated with the client device, a circuit configured to produce a vibration test prompt on the at least one handle, and a plurality of sensors integrated in the client device, plurality of sensors including at least one pressure sensor integrated with the at least one handle, a movement sensor, a voice recognition system, a touchscreen, a camera, and a touchscreen;
receiving information from the plurality of sensors indicative of a user input response to the test prompts, the information including at least one of:
data indicative of movement of the client device,
image data capturing the position of the patient's eyes,
image data capturing the pupils of eyes of the patient,
touch data indicative of the patient's peripheral vision,
image data capturing the patient's face,
grip pressure data,
touch data selecting a displayed target,
audio data or touch data responsive to the vibration test prompt,
audio data indicative of clarity of speech,
audio data or touch data input data representing identifying objects provided on the display, and
audio data or touch data indicative of the number of objects provided on the display; and
generating, by the processor, response information indicative of the information received from the plurality of sensors.

20. The method of claim 19, further comprising sending, by the client device, the generated response information over a communications network to a control device for further processing.

* * * * *